United States Patent
Eastman et al.

(10) Patent No.: US 9,938,271 B2
(45) Date of Patent: Apr. 10, 2018

(54) INHIBITORS OF HUMAN IMMUNODEFICIENCY VIRUS REPLICATION

(71) Applicant: VIIV HEALTHCARE UK (NO. 5) LIMITED, Brentford, Middlesex (GB)

(72) Inventors: Kyle J. Eastman, Wallingford, CT (US); John F. Kadow, Wallingford, CT (US); B. Narasimhulu Naidu, Wallingford, CT (US); Kyle E. Parcella, Wallingford, CT (US); Kevin Peese, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/119,465

(22) PCT Filed: Feb. 13, 2015

(86) PCT No.: PCT/US2015/015933
§ 371 (c)(1),
(2) Date: Aug. 17, 2016

(87) PCT Pub. No.: WO2015/126765
PCT Pub. Date: Aug. 27, 2015

(65) Prior Publication Data
US 2017/0008887 A1     Jan. 12, 2017

Related U.S. Application Data

(60) Provisional application No. 61/941,619, filed on Feb. 19, 2014.

(51) Int. Cl.
*C07D 471/04* (2006.01)
*C07D 498/22* (2006.01)

(52) U.S. Cl.
CPC ......... *C07D 471/04* (2013.01); *C07D 498/22* (2013.01)

(58) Field of Classification Search
None
See application file for complete search history.

(56) References Cited

FOREIGN PATENT DOCUMENTS

| WO | WO 2010/130034 A1 | 11/2010 |
|----|-------------------|---------|
| WO | WO 2013/157622 A1 | 10/2013 |
| WO | WO 2014/159959 A1 | 10/2014 |

*Primary Examiner* — Noble E Jarrell
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

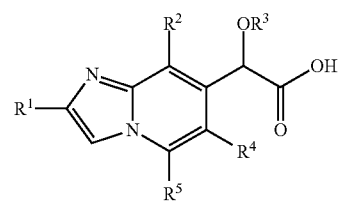

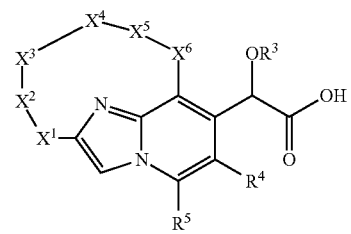

11 Claims, No Drawings

INHIBITORS OF HUMAN IMMUNODEFICIENCY VIRUS REPLICATION

CROSS-REFERENCE TO RELATED APPLICATIONS

This application is a 371 of International Application No. PCT/US2015/015933, filed 13 Feb. 2015, which claims the benefit of U.S. Provisional Application No. 61/941,619, filed 19 Feb. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963, WO2012066442, WO2014021867, WO20140028384, WO2014164428, WO2014164409, and WO2014159959.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

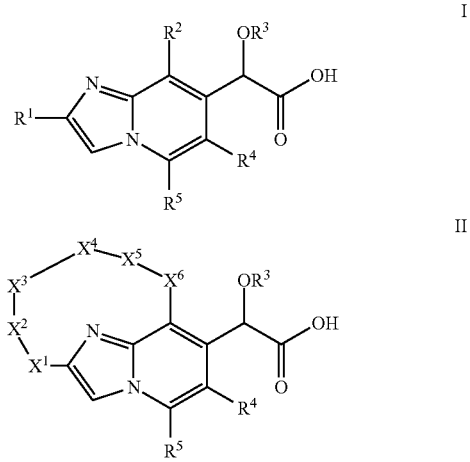

where:
$R^1$ is phenyl substituted with 0-3 substituents selected from halo, alkyl, haloalkyl, alkenyl, $Ar^1$, $(Ar^1)$alkyl, and $(Ar^1)O$;

$R^2$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or $R^2$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

$R^3$ is alkyl or haloalkyl;

$R^4$ is alkyl;

$R^5$ is hydrogen or alkyl;

$R^6$ is $Ar^1$ or $(Ar^1)$alkyl;

$R^7$ is hydrogen or alkyl; and $Ar^1$ is phenyl or pyridinyl and is substituted with 0-3 substituents selected from halo, cyano, alkyl, haloalkyl, alkoxy, haloalkoxy, and alkenyloxy;

$X^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;

$X^2$ is phenyl substituted with 0-3 substituents selected from halo, alkyl, haloalkyl, alkoxy, and haloalkoxy;

$X^3$ is O or absent;

$X^4$ is alkylene or alkenylene; $X^5$ is O or absent; and $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;

or a pharmaceutically acceptable salt thereof.

Another aspect of the invention is a compound according to Formula I where $R^1$ is phenyl substituted with 0-3 substituents selected from halo, alkyl, haloalkyl, alkenyl, $Ar^1$, $(Ar^1)$alkyl, and $(Ar^1)$O; $R^2$ is piperidinyl substituted with 0-3 alkyl substituents or $R^2$ is chromanyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; $R^3$ is alkyl; $R^4$ is alkyl; $R^5$ is hydrogen; and $Ar^1$ is phenyl substituted with 0-3 substituents selected from halo, cyano, alkyl, haloalkyl, alkoxy, haloalkoxy, and alkenyloxy; or a pharmaceutically acceptable salt thereof.

Another aspect of the invention is a compound according to Formula II where $X^1$ is phenyl; $X^2$ is phenyl substituted with 0-3 substituents selected from halo, alkyl, haloalkyl, alkoxy, and haloalkoxy; $X^3$ is O or absent; $X^4$ is alkylene or alkenylene; $X^5$ is O or absent; and $X^6$ is piperidinyl substituted with 0-3 alkyl substituents; or a pharmaceutically acceptable salt thereof.

Another aspect of the invention is a compound according to Formula I where $R^1$ is phenyl substituted with 0-3 substituents selected from halo, alkyl, haloalkyl, alkenyl, $Ar^1$, $(Ar^1)$alkyl, and $(Ar^1)$O.

Another aspect of the invention is a compound according to Formula I where $R^2$ is piperidinyl substituted with 0-3 alkyl substituents.

Another aspect of the invention is a compound according to Formula I where $R^2$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound according to Formula I where $R^2$ is chromanyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound according to Formula I where $R^3$ is alkyl, $R^4$ is alkyl, and $R^5$ is hydrogen.

Another aspect of the invention is a compound according to Formula I where $Ar^1$ is phenyl substituted with 0-3 substituents selected from halo, cyano, alkyl, haloalkyl, alkoxy, haloalkoxy, and alkenyloxy.

Another aspect of the invention is a compound according to Formula II where $X^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl.

Another aspect of the invention is a compound according to Formula II where $X^1$ is phenyl.

Another aspect of the invention is a compound according to Formula II where $X^2$ is phenyl substituted with 0-3 substituents selected from halo, alkyl, haloalkyl, alkoxy, and haloalkoxy.

Another aspect of the invention is a compound according to Formula II where $X^3$ is O or absent, $X^4$ is alkylene or alkenylene, and $X^5$ is O or absent.

Another aspect of the invention is a compound according to Formula II where $X^3$ is absent, $X^4$ is alkylene or alkenylene, and $X^5$ is absent.

Another aspect of the invention is a compound according to Formula II where $X^6$ is piperidinyl substituted with 0-3 alkyl substituents;

For a compound of Formula I, the scope of any instance of a variable substituent, including $R^1$, $R^2$, $R^3$, $R^4$, $R^5$, $R^6$, $R^7$, $Ar^1$, $X^1$, $X^2$, $X^3$, $X^4$, $X^5$, and $X^6$, can be used independently with the scope of any other instance of a variable substituent. As such, the invention includes combinations of the different aspects.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC 18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Example | $EC_{50}$ μM |
|---------|--------------|
| 1 | 0.016 |
| 2 | 0.187 |
| 3 | 0.011 |
| 4 | 0.265 |
| 5 | 0.034 |
| 6 | 0.56 |
| 7 | 0.019 |
| 8 | 0.01 |
| 9 | 0.036 |
| 10 | 0.148 |

Pharmaceutical Composition and Methods of Use

The compounds of this invention inhibit HIV replication. Accordingly, another aspect of the invention is a method for treating HIV infection in a human patient comprising the administration of a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "CH$_3$CN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I.

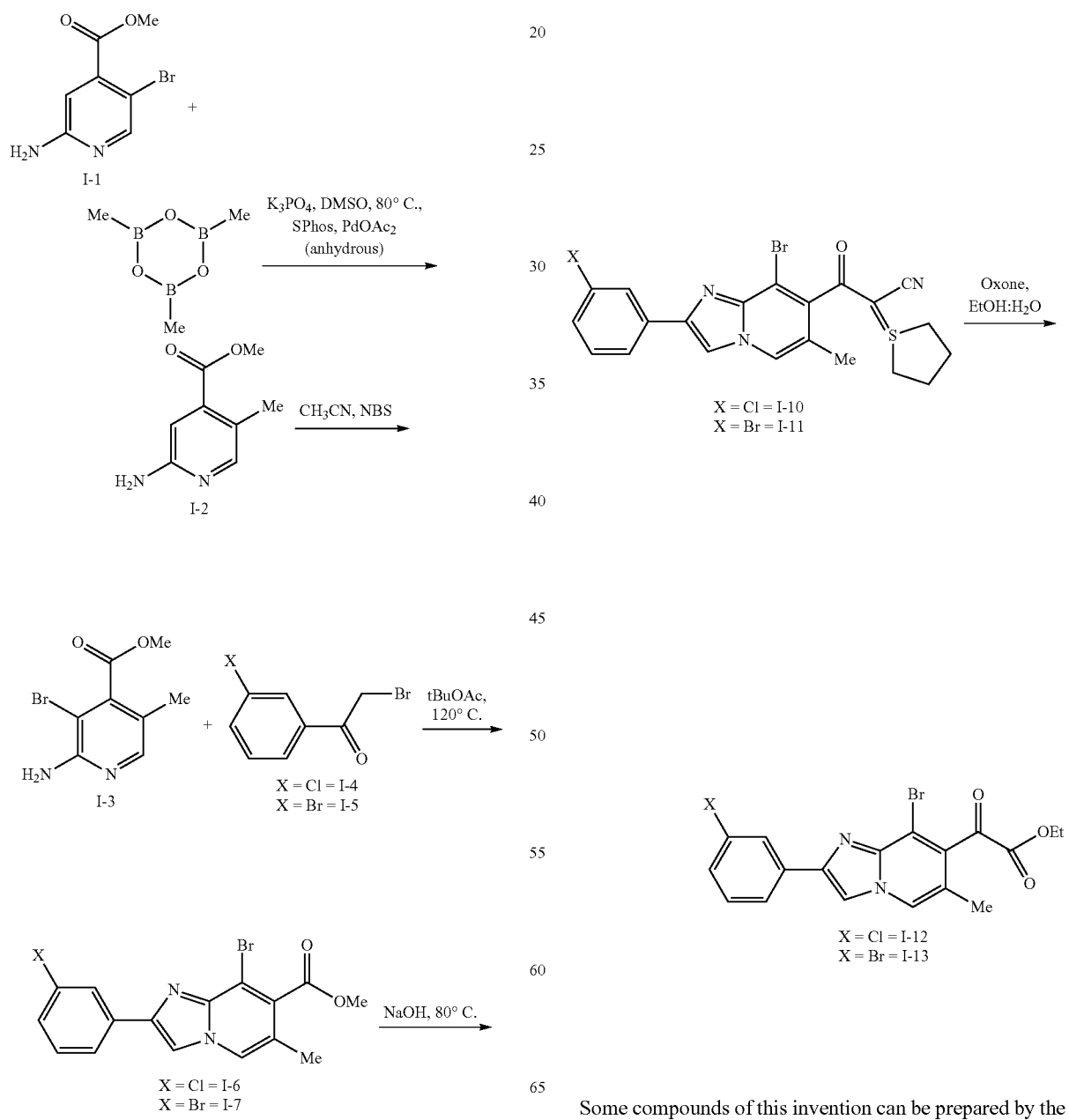

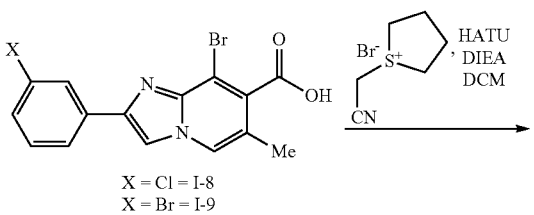

Some compounds of this invention can be prepared by the methods outlined in the Scheme II.

Scheme II
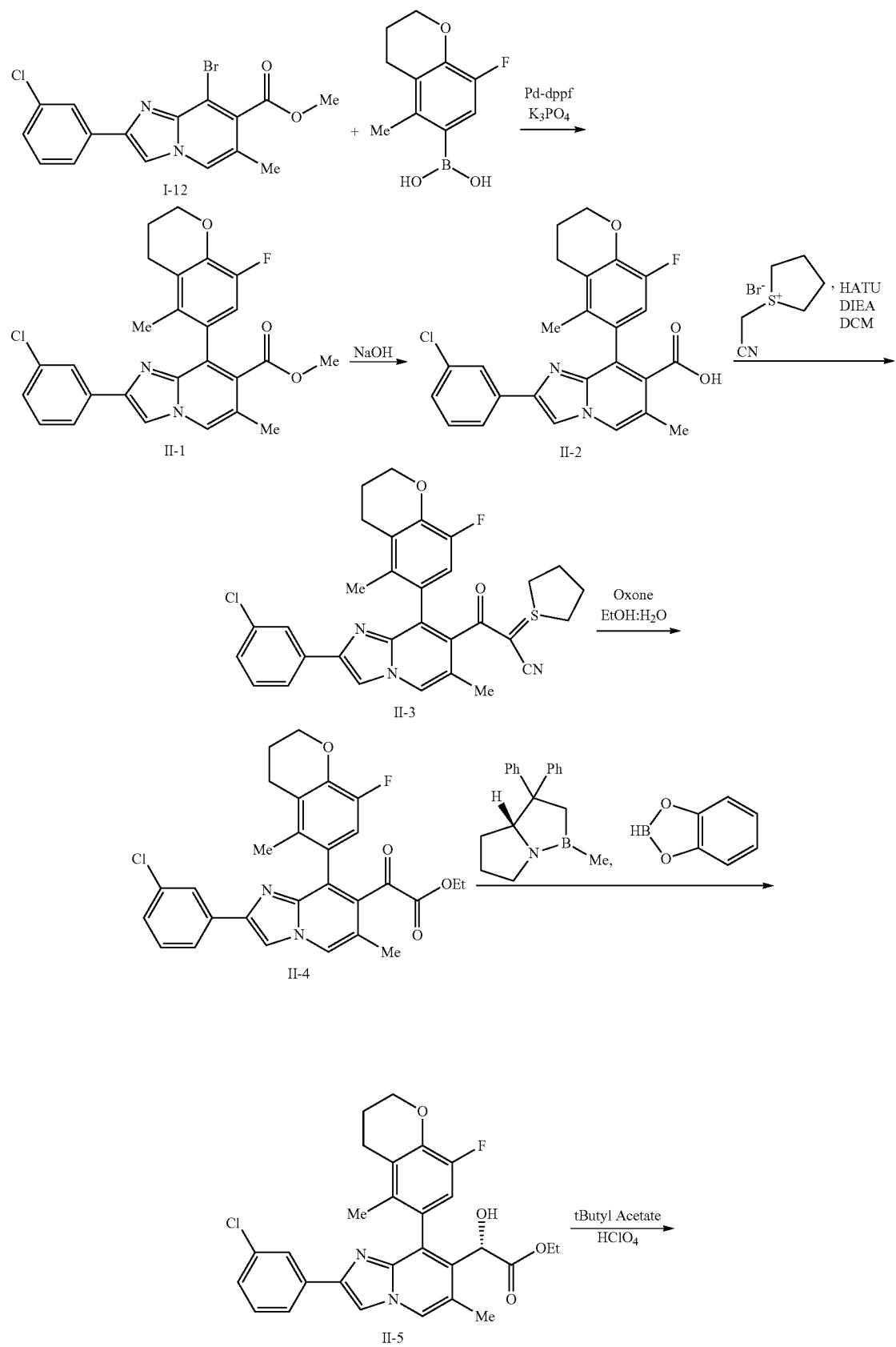

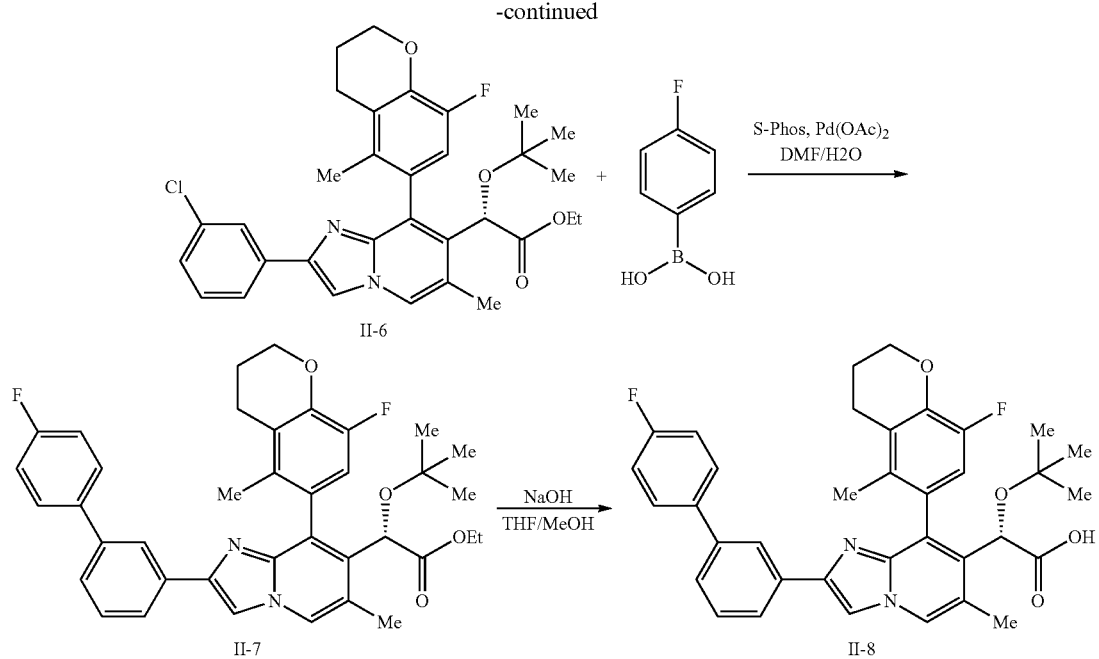
Some compounds of this invention can be prepared by the methods outlined in the Scheme III.
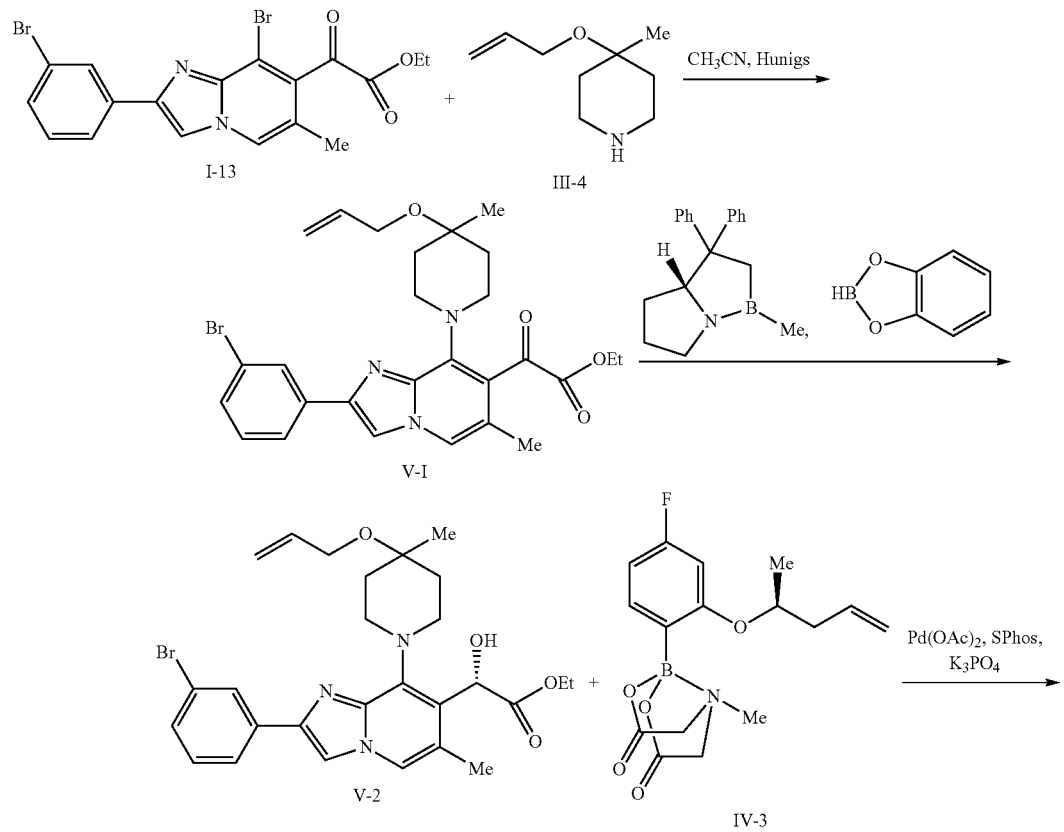

-continued
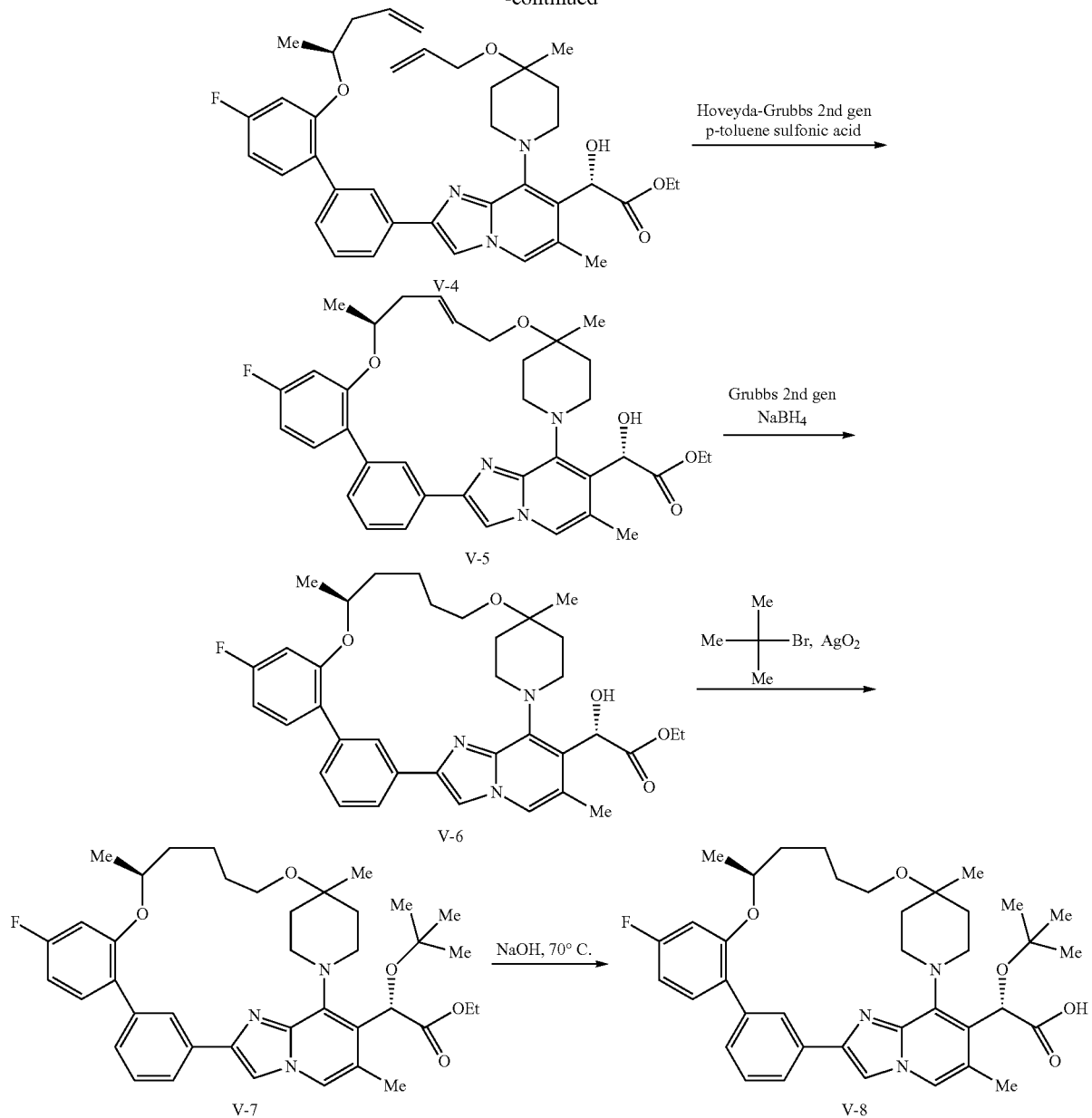
Some compounds of this invention can be prepared by the methods outlined in the Scheme IV.
Scheme IV
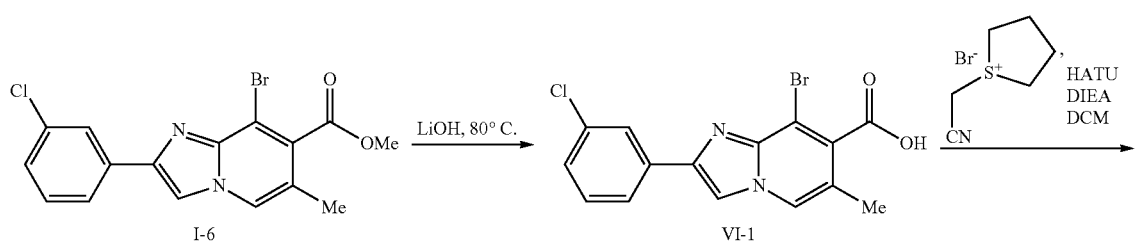

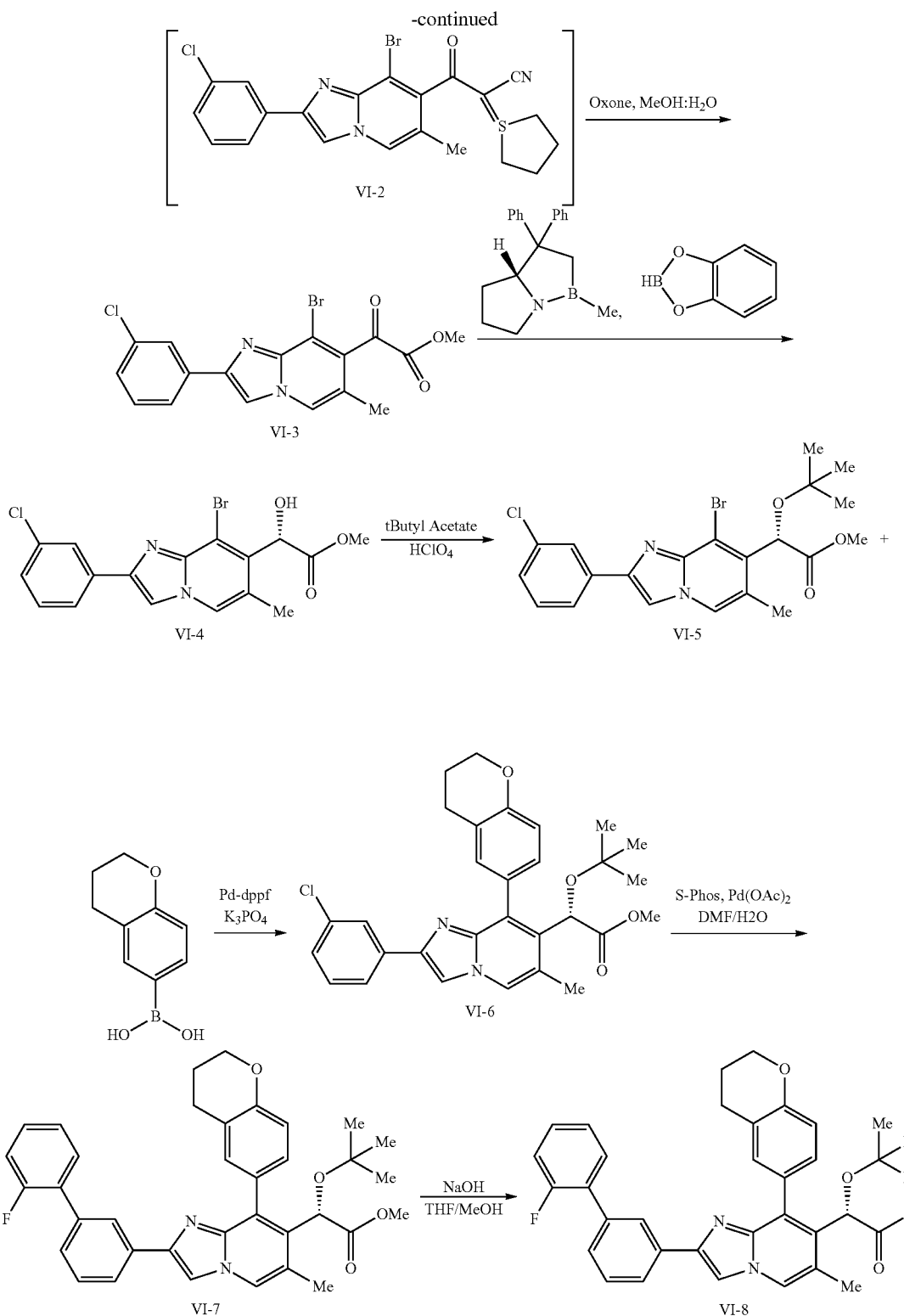

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H$_2$O/acetonitrile with 10 mM NH$_4$OAc and mobile phase B:A: 9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

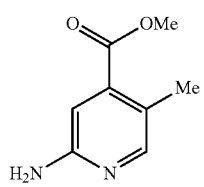

Methyl 2-amino-5-methylisonicotinate

Methyl 2-amino-5-bromoisonicotinate (12.3 g, 53.2 mmol), dicyclohexyl(2',6'-dimethoxy-[1,1'-biphenyl]-2-yl)phosphine (4.37 g, 10.7 mmol), tripotassium phosphate (crushed) (22.6 g, 106 mmol), diacetoxypalladium (1.20 g, 5.32 mmol), were combined, degassed and backfilled with $N_2$ and then dissolved in DMSO (266 ml) and trimethylboroxine (25.0 g, 199 mmol) at rt. The mixture was then heated to 80° C. and allowed to stir overnight. The mixture was then diluted with EtOAc and washed with $H_2O$. The organic phase was dried over $Na_2SO_4$, filtered, absorbed onto celite and was purified on silica gel (Biotage, 300 g column, EtOAc/hexanes gradient, fraction collection at λ=254 nm) to give crude product as an orange oil (13 g). The oil was triturated with $Et_2O$ to isolate 3 g of clean white solid. The mother liquor (9 g) was repurified on a on silica gel (Biotage, 220 g column, EtOAc/hexanes gradient, fraction collection at λ=254 nm) to give 5 g of material for a total of 8 g of the expected product: methyl 2-amino-5-methylisonicotinate (8.0 g, 48 mmol, 90% yield). $^1$H NMR (500 MHz, DMSO-d6) δ 7.87 (s, 1H), 6.82 (s, 1H), 6.00 (s, 2H), 3.81 (s, 3H), 2.23 (d, J=0.5 Hz, 3H). LC-MS retention time: 0.689 min; m/z (MH+): 167. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

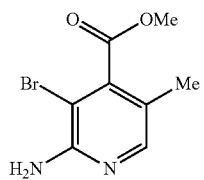 [SMILES: COC(=O)c1c(C)cnc(N)c1Br]

Methyl 2-amino-3-bromo-5-methylisonicotinate

1-Bromopyrrolidine-2,5-dione (2.24 g, 12.6 mmol) was added to a stirring solution of methyl 2-amino-5-methylisonicotinate (1.90 g, 11.4 mmol) in acetonitrile (114 ml) at rt. The reaction was allowed to stir at rt for 30 min. The reaction was then concentrated, adsorbed onto Celite and was purified on silica gel (Biotage, EtOAc/hexanes gradient, fraction collection at λ=254 nm) to give the expected product methyl 2-amino-3-bromo-5-methylisonicotinate (1.90 g, 7.75 mmol, 67% yield). $^1$H NMR (500 MHz, METHANOL-d4) δ 7.83 (d, J=0.6 Hz, 1H), 3.94 (s, 3H), 2.12 (d, J=0.8 Hz, 3H). LC-MS retention time: 0.749 min; m/z (MH+): 245, 247. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

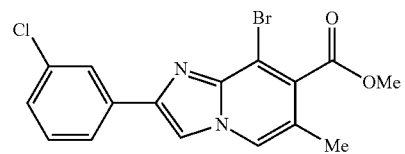

Methyl 8-bromo-2-(3-chlorophenyl)-6-methylimidazo[1,2-a]pyridine-7-carboxylate

Methyl 2-amino-3-bromo-5-methylisonicotinate (3.93 g, 16.0 mmol) was dissolved in tBuOAc (100 ml). To this mixture was added 2-bromo-1-(3-chlorophenyl)ethanone (4.49 g, 19.2 mmol). The mixture was heated to 120° C. in a 250 mL round bottom flask equipped with a vigreux column. The reaction was allowed to stir for 3 h. After this time, the reaction was cooled to rt. The mixture was diluted with EtOAc and washed with sat aq NaHCO$_3$, and sat aq NaCl. The organic phase was dried over Na$_2$SO$_4$, filtered, concentrated, absorbed onto Celite and purified on silica gel (Biotage 330 g column, EtOAc/hexanes gradient, fraction collection at λ=254 nm) to give the expected product methyl 8-bromo-2-(3-chlorophenyl)-6-methylimidazo[1,2-a]pyridine-7-carboxylate (4.25 g, 11.2 mmol, 70% yield). $^1$H NMR (500 MHz, DMSO-d6) δ 8.64 (s, 1H), 8.52 (d, J=1.1 Hz, 1H), 8.05 (t, J=1.8 Hz, 1H), 7.97 (dt, J=7.8, 1.2 Hz, 1H), 7.54-7.47 (m, 1H), 7.42 (ddd, J=8.0, 2.1, 1.1 Hz, 1H), 3.95 (s, 3H), 2.24 (d, J=0.9 Hz, 3H). LC-MS retention time: 1.26 min; m/z (MH+): 381. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

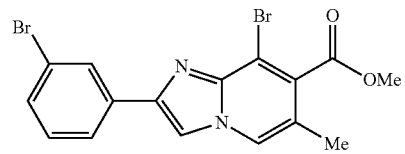 [SMILES: COC(=O)c1c(C)cn2cc(-c3cccc(Cl)c3)nc2c1Br]

Methyl 8-bromo-2-(3-bromophenyl)-6-methylimidazo[1,2-a]pyridine-7-carboxylate Methyl 2-amino-3-bromo-5-methylisonicotinate (11.8 g, 48.1 mmol) was dissolved in tBuOAc (150 ml). To this mixture was added 2-bromo-1-(3-bromophenyl)ethanone (16.1 g, 57.8 mmol). The mixture was heated to 120° C. in a sealed vessel. After 11 h, the reaction mixture was cooled to rt. The mixture was then diluted with EtOAc and washed with sat aq bicarb. The layers were separated and the aq layer was extracted with EtOAc (2×50 mL). The combined organic extracts were washed with water, brine, dried over $Na_2SO_4$, filtered and concentrated to give a yellow solid. This solid was adsorbed onto Celite and then purified on silica gel eluting with 0-65% EtOAc in hexanes gradient over 15 CV to give methyl 8-bromo-2-(3-bromophenyl)-6-methylimidazo[1,2-a]pyridine-7-carboxylate (15 g, 35 mmol, 74% yield). $^1$H NMR (400 MHz, $CDCl_3$) δ 8.14 (t, J=1.7 Hz, 1H), 7.92 (d, J=1.1 Hz, 1H), 7.91-7.88 (m, 1H), 7.87 (s, 1H), 7.47 (ddd, J=8.0, 2.0, 1.1 Hz, 1H), 7.30 (t, J=7.9 Hz, 1H), 4.02 (s, 3H), 2.32 (s, 3H). LC-MS retention time: 1.27 min; m/z (MH+): 425. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

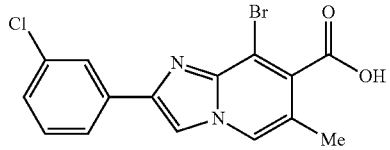 [SMILES: Cc1cn2cc(-c3cccc(Cl)c3)nc2c(Br)c1C(=O)O]

8-Bromo-2-(3-chlorophenyl)-6-methylimidazo[1,2-a]pyridine-7-carboxylic acid

Sodium hydroxide (55.3 ml, 55.3 mmol, 1M aq) was added to a stirring solution of methyl 8-bromo-2-(3-chlorophenyl)-6-methylimidazo[1,2-a]pyridine-7-carboxylate (4.20 g, 11.1 mmol) in MeOH (55.3 ml), THF (55.3 ml) at rt. The reaction mixture was equipped with a vigreux column, heated to 80° C. and allowed to stir at this temp for 6 h, the heating bath was removed and the mixture was allowed to stir overnight at rt. The reaction mixture was heated once more to 80° C. and stirred at this temp for 1 h. The reaction mixture was finally allowed to cool to rt and then diluted with EtOAc and washed with 1M HCl. A white ppt had formed in the aq layer. The aq layer was filtered and the ppt was isolated. The organic phase was concentrated to give a white solid which was combined with the ppt from the aq layer. The combined product was azeotroped with toluene 2× to give the expected product 8-bromo-2-(3-chlorophenyl)-6-methylimidazo[1,2-a]pyridine-7-carboxylic acid (4.0 g, 11 mmol, 99% yield). $^1$H NMR (500 MHz, DMSO-d6) δ 14.04 (br. s, 1H), 8.60 (s, 1H), 8.48 (d, J=1.1 Hz, 1H), 8.04 (t, J=1.8 Hz, 1H), 7.96 (dt, J=8.0, 1.2 Hz, 1H), 7.53-7.46 (m, 1H), 7.44-7.38 (m, 1H), 2.28 (d, J=0.9 Hz, 3H). LC-MS retention time: 0.889 min; m/z (MH+): 367. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

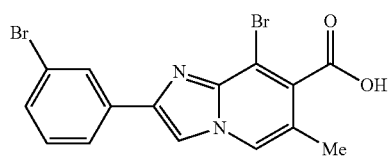

8-Bromo-2-(3-bromophenyl)-6-methylimidazo[1,2-a]pyridine-7-carboxylic acid

Methyl 8-bromo-2-(3-bromophenyl)-6-methylimidazo[1,2-a]pyridine-7-carboxylate (3.8 g, 8.9 mmol) was taken up in a 1:1:1 mixture of THF (40 mL):Methanol (40 mL):1M NaOH (40 ml, 40.0 mmol) and heated to 80° C. The solution was allowed to stir at this temp for 10 h. At this point the solution was cooled to rt and diluted with 60 mL of 1 M HCl, resulting immediately in a heavy white ppt. The mixture was concentrated to an aq mixture and the solids were filtered rinsing with 500 mL of water. The solids were then azeotroped with Toluene (3×30 mL) to give 8-bromo-2-(3-bromophenyl)-6-methylimidazo[1,2-a]pyridine-7-carboxylic acid (3.8 g, 9.3 mmol, >100% yield) as a white solid. $^1$H NMR (400 MHz, DMSO-d6) δ 14.04 (br. s., 1H), 8.60 (s, 1H), 8.47 (d, J=1.1 Hz, 1H), 8.18 (t, J=1.7 Hz, 1H), 7.99 (dt, J=8.0, 1.1 Hz, 1H), 7.54 (ddd, J=7.9, 2.0, 0.9 Hz, 1H), 7.42 (t, J=7.9 Hz, 1H), 2.28 (d, J=1.1 Hz, 3H). LC-MS retention time: 0.915 min; m/z (MH+): 411. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

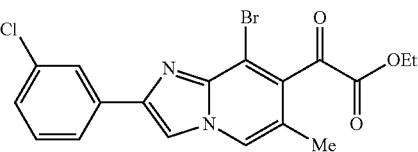

Ethyl 2-(8-bromo-2-(3-chlorophenyl)-6-methylimidazo[1,2-a]pyridin-7-yl)-2-oxoacetate Step 1: DIEA (5.88 ml, 33.6 mmol) was added to a stirring solution of 8-bromo-2-(3-chlorophenyl)-6-methylimidazo

[1,2-a]pyridine-7-carboxylic acid (4.1 g, 11 mmol), HATU (5.12 g, 13.5 mmol),1-(cyanomethyl)tetrahydro-1H-thiophen-1-ium bromide (4.67 g, 22.4 mmol) in DCM (112 ml) at rt and the reaction mixture was allowed to stir at rt for 5 h. The reaction was diluted with EtOAc and washed with sat. aq. NaHCO$_3$. The organic phase was concentrated, adsorbed onto Celite and was purified on silica gel (Biotage, EtOAc/hexanes gradient followed by MeOH/DCM gradient, fraction collection at λ=254 nm) to give 3-[8-bromo-2-(3-chlorophenyl)-6-methylimidazo[1,2-a]pyridin-7-yl]-3-oxo-2-(1λ$^4$-thiolan-1-ylidene)propanenitrile (3.7 g, 7.8 mmol, 70% yield). LC-MS retention time: 0.939 min; m/z (MH+): 476. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: 3-[8-Bromo-2-(3-chlorophenyl)-6-methylimidazo[1,2-a]pyridin-7-yl]-3-oxo-2-(1λ$^4$-thiolan-1-ylidene)propanenitrile (3.10 g, 6.53 mmol) was taken up in EtOH (115 ml) and water (11.5 ml) and treated with Oxone (20.0 g, 32.6 mmol) at rt. The heterogeneous mixture was allowed to stir for 2 h. The mixture was diluted with EtOAc and neutralized with sat aq NaHCO$_3$. The layers were separated, the organic phase dried over Na$_2$SO$_4$, filtered, concentrated and adsorbed onto Celite and was purified on silica gel (Biotage, EtOAc/hexanes gradient, fraction collection at λ=254 nm) to give ethyl 2-(8-bromo-2-(3-chlorophenyl)-6-methylimidazo[1,2-a]pyridin-7-yl)-2-oxoacetate (1.18 g, 2.80 mmol, 43% yield). $^1$H NMR (500 MHz, DMSO-d6) δ 8.70 (s, 1H), 8.56 (d, J=1.1 Hz, 1H), 8.06 (t, J=1.8 Hz, 1H), 7.98 (dt, J=7.9, 1.3 Hz, 1H), 7.53-7.48 (m, 1H), 7.46-7.42 (m, 1H), 4.38 (q, J=7.1 Hz, 2H), 2.21 (d, J=0.9 Hz, 3H), 1.30 (t, J=7.1 Hz, 3H). LC-MS retention time: 1.36 min; m/z (MH+): 423. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

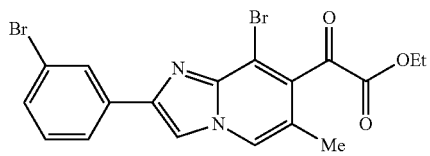 [SMILES: CCOC(=O)C(=O)c1c(C)cn2cc(-c3cccc(Cl)c3)nc2c1Br]

Ethyl 2-(8-bromo-2-(3-bromophenyl)-6-methylimidazo[1,2-a]pyridin-7-yl)-2-oxoacetate Step 1: DIEA (4.86 mL, 27.8 mmol) was added to a stirring solution of 8-bromo-2-(3-bromophenyl)-6-methylimidazo[1,2-a]pyridine-7-carboxylic acid (3.8 g, 9.3 mmol) and HATU (4.23 g, 11.1 mmol) in DCM (93 mL) at rt. After 10 min of stirring the heavy white ppt slowly dissolved. Next, 1-(cyanomethyl)tetrahydro-1H-thiophen-1-ium bromide (1.9 g, 9.3 mmol) was added in a single aliquot. LCMS after 2 h indicates approximately 90% conversion. The mixture was diluted with NH$_4$Cl aq and DCM. The layers were separated and the aq layer was extracted with DCM (2×20 mL) and concentrated to give an orange solid. This solid was flashed on silica gel (Biotage) first eluting with a 0-100% EtOAc in hexanes gradient over 12 CV to remove all non-polar biproducts. Next, the column was eluted with a 0-10% MeOH in DCM graient over 12 CV to give 3-[8-bromo-2-(3-bromophenyl)-6-methylimidazo[1,2-a]pyridin-7-yl]-3-oxo-2-(1λ$^4$-thiolan-1-ylidene)propanenitrile (3.1 g, 5.9 mmol, 64% yield) as a yellow solid. LC-MS retention time: 0.957 min; m/z (MH+): 520. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: 3-[8-Bromo-2-(3-bromophenyl)-6-methylimidazo[1,2-a]pyridin-7-yl]-3-oxo-2-(1λ$^4$-thiolan-1-ylidene)propanenitrile (2.8 g, 5.4 mmol) was taken up in EtOH (50 ml) and Water (5 ml) and treated with Oxone (19.9 g, 32.4 mmol) at rt. The heterogeneous mixture was allowed to stir for 2 h. The mixture was diluted with EtOAc and neutralized with sat. aq. NaHCO$_3$. The organic phase was concentrated and adsorbed onto Celite and was purified on silica gel (Biotage, EtOAc/hexanes gradient, fraction collection at λ=254 nm) to give ethyl 2-(8-bromo-2-(3-chlorophenyl)-6-methylimidazo[1,2-a]pyridin-7-yl)-2-oxoacetate (0.650 g, 1.58 mmol, 30% yield). $^1$H NMR (500 MHz, CDCl$_3$) δ 8.15 (t, J=1.7 Hz, 1H), 7.98 (d, J=1.1 Hz, 1H), 7.93 (s, 1H), 7.91 (dq, J=7.8, 0.9 Hz, 1H), 7.49 (ddd, J=8.0, 2.0, 1.1 Hz, 1H), 7.32 (t, J=7.9 Hz, 1H), 4.45 (q, J=7.2 Hz, 2H), 2.29 (d, J=1.1 Hz, 3H), 1.42 (t, J=7.2 Hz, 3H). LC-MS retention time: 1.38 min; m/z (MH+): 467. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

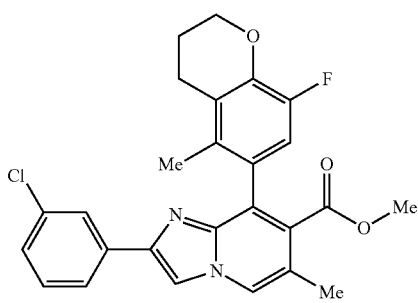 [SMILES: COC(=O)c1c(C)cn2cc(-c3cccc(Cl)c3)nc2c1-c1cc(F)c2c(c1C)CCCO2]

Methyl 2-(3-chlorophenyl)-8-(8-fluoro-5-methyl-chroman-6-yl)-6-methylimidazo[1,2-a]pyridine-7-carboxylate Methyl 8-bromo-2-(3-chlorophenyl)-6-methylimidazo[1,2-a]pyridine-7-carboxylate (200 mg, 0.527 mmol), (8-fluoro-5-methylchroman-6-yl)boronic acid (133 mg, 0.632 mmol), tripotassium phosphate (335 mg, 1.58 mmol), PdCl$_2$(dppf) (39 mg, 0.053 mmol) were combined in DMF (10.5 ml) at rt. The mixture was degassed, backfilled with N$_2$ and warmed to 60° C. and allowed to stir at this temperature overnight. The reaction mixture was then concentrated, adsorbed onto Celite and was purified on silica gel (Biotage, EtOAc/hexanes gradient, fraction collection at λ=254 nm) to give methyl 2-(3-chlorophenyl)-8-(8-fluoro-5-methylchroman-6-yl)-6-methylimidazo[1,2-a]pyridine-7-carboxylate (162 mg, 0.348 mmol, 66% yield). LC-MS retention time: 1.14 min; m/z (MH+): 465. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

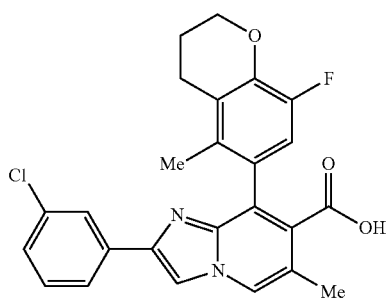 [SMILES: Cc1cn2cc(-c3cccc(Cl)c3)nc2c(-c2cc(F)c3c(c2C)CCCO3)c1C(=O)O]

2-(3-Chlorophenyl)-8-(8-fluoro-5-methylchroman-6-yl)-6-methylimidazo[1,2-a]pyridine-7-carboxylic acid Sodium hydroxide (2.65 ml, 2.65 mmol, 1M aq) was added to a stirring solution of methyl 2-(3-chlorophenyl)-8-(8-fluoro-5-methylchroman-6-yl)-6-methylimidazo[1,2-a]pyridine-7-carboxylate (246 mg, 0.529 mmol) in MeOH (2.65 ml), THF (2.65 ml) at rt. The reaction was heated to 65° C. and allowed to stir for 2 hr and then warmed to 80° C. and allowed to stir for 16 hr overnight. The mixture was then diluted with EtOAc and washed with 1M aq HCl, and sat aq NaCl. The organic phase was dried over Na$_2$SO$_4$, filtered and concentrated to give the expected product 2-(3-chlorophenyl)-8-(8-fluoro-5-methylchroman-6-yl)-6-methylimidazo[1,2-a]pyridine-7-carboxylic acid (135 mg, 0.299 mmol, 57% yield). LC-MS retention time: 0.979 min; m/z (MH+): 451. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

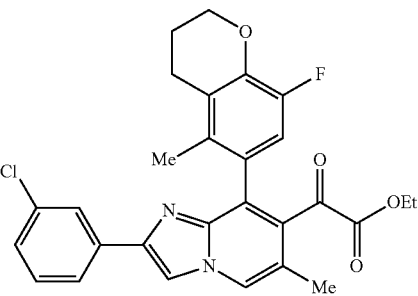 [SMILES: CCOC(=O)C(=O)c1c(C)cn2cc(-c3cccc(Cl)c3)nc2c1-c1cc(F)c2c(c1C)CCCO2]

Ethyl 2-(2-(3-chlorophenyl)-8-(8-fluoro-5-methyl-chroman-6-yl)-6-methylimidazo[1,2-a]pyridin-7-yl)-2-oxoacetate Step 1: DIEA (157 μl, 0.898 mmol) was added to a stirring solution of 2-(3-chlorophenyl)-8-(8-fluoro-5-methylchroman-6-yl)-6-methylimidazo[1,2-a]pyridine-7-carboxylic acid (135 mg, 0.299 mmol), HATU (137 mg, 0.359 mmol), 1-(cyanomethyl)tetrahydro-1H-thiophen-1-ium bromide (125 mg, 0.599 mmol), and DMAP (3 mg, 0.03 mmol) in DCM (3 ml) at rt and the reaction mixture was allowed to stir at rt. After 15 min of stirring, 36 mg of DMAP was added along with 63 mg of 1-(cyanomethyl)tetrahydro-1H-thiophen-1-ium bromide. The reaction was allowed to stir for 1 h. After this time, 63 mg more of 1-(cyanomethyl)tetrahydro-1H-thiophen-1-ium bromide was added along with more DIEA (157 μl, 0.898 mmol). After another 1 h of stirring. 63 mg more of 1-(cyanomethyl)tetrahydro-1H-thiophen-1-ium bromide was added and the reaction was allowed to stir for 1 additional h. The reaction was then concentrated, adsorbed onto Celite and was purified on silica gel (Biotage, using a EtOAc/Hex gradient followed by a MeOH/DCM gradient to give 156 mg (0.279 mmol) of the expected glide intermediate. LC-MS retention time: 0.967 min; m/z (MH+): 560. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: 3-[2-(3-Chlorophenyl)-8-(8-fluoro-5-methyl-3,4-dihydro-2H-1-benzopyran-6-yl)-6-methylimidazo[1,2-a]pyridin-7-yl]-3-oxo-2-[(1Z)-1λ⁴-thiolan-1-ylidene]propanenitrile (156 mg, 0.279 mmol) was taken up in EtOH (5 ml) and water (0.5 ml) and treated with Oxone (856 mg, 1.39 mmol) at rt. The reaction mixture was allowed to stir for 7 h. The pH of solution is approximately) at this point. DIEA (1 mL) was added to the reaction mixture to neutralize the pH. The reaction was concentrated, adsorbed onto Celite and was purified on silica gel (Biotage, EtOAc/hexanes gradient, fraction collection at λ=254 nm) to give the expected product ethyl 2-(2-(3-chlorophenyl)-8-(8-fluoro-5-methylchroman-6-yl)-6-methylimidazo[1,2-a]pyridin-7-yl)-2-oxoacetate (43 mg, 0.085 mmol, 31% yield). $^1$H NMR (500 MHz, DMSO-d6) δ 8.63 (s, 1H), 8.56-8.52 (m, 1H), 7.93-7.89 (m, 1H), 7.87-7.83 (m, 1H), 7.48-7.42 (m, 1H), 7.40-7.36 (m, 1H), 6.87-6.80 (m, 1H), 4.30-4.18 (m, 2H), 3.85-3.74 (m, 2H), 3.01-2.98 (m, 1H), 2.80-2.73 (m, 1H), 2.28 (d, J=0.9 Hz, 3H), 2.08-2.05 (m, 2H), 1.82 (s, 3H), 1.03 (s, 3H). LC-MS retention time: 1.27 min; m/z (MH+): 507. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

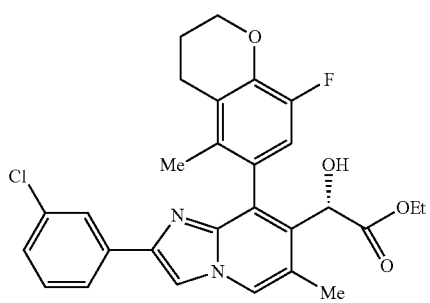 [SMILES: CCOC(=O)[C@@H](O)c1c(C)cn2cc(-c3cccc(Cl)c3)nc2c1-c1cc(F)c2c(c1C)CCCO2]

(2S)-Ethyl 2-(2-(3-chlorophenyl)-8-(8-fluoro-5-methylchroman-6-yl)-6-methylimidazo[1,2-a]pyridin-7-yl)-2-hydroxyacetate (R)-1-Methyl-3,3-diphenylhexahydropyrrolo[1,2-c][1,3,2]oxazaborole (1M in toluene) (25 μl, 0.024 mmol) was added to a solution of ethyl 2-(2-(3-chlorophenyl)-8-(8-fluoro-5-methylchroman-6-yl)-6-methylimidazo[1,2-a]pyridin-7-yl)-2-oxoacetate (31 mg, 0.061 mmol) in toluene (1.2 ml) at rt. The mixture was cooled to −35° C. and treated with catecholborane (50% in toluene) (21 μl, 0.086 mmol). The reaction mixture was allowed to stir for 1.5 h. Then an additional amount of (R)-1-methyl-3,3-diphenylhexahydropyrrolo[1,2-c][1,3,2]oxazaborole (1M in toluene) (25 μl, 0.024 mmol) followed by catecholborane (50% in toluene) (21 μl, 0.086 mmol) was added. The reaction was placed in the freezer (−30° C.) for 16 h overnight. The reaction was quenched with 2M aq Na2CO3 and was then diluted with EtOAc and stirred for 15 min. The mixture was diluted with ethyl acetate and washed with 2M aq Na2CO3, and sat aq NaCl. The organic phase was dried over Na2SO4, filtered and concentrated adsorbing onto Celite and was purified on silica gel (Biotage, EtOAc/hexanes gradient, fraction collection at λ=254 nm) to give the expected product (2S)-ethyl 2-(2-(3-chlorophenyl)-8-(8-fluoro-5-methylchroman-6-yl)-6-methylimidazo[1,2-a]pyridin-7-yl)-2-hydroxyacetate (20 mg, 0.039 mmol, 64% yield). LC-MS retention time: 1.06 min; m/z (MH+): 509. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

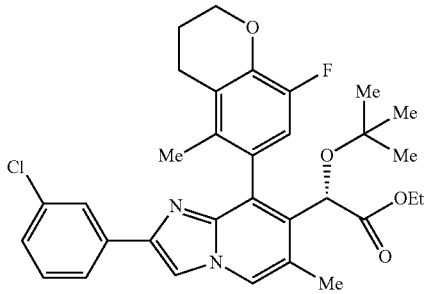 [SMILES: CCOC(=O)[C@@H](OC(C)(C)C)c1c(C)cn2cc(-c3cccc(Cl)c3)nc2c1-c1cc(F)c2c(c1C)CCCO2]

(2S)-Ethyl 2-(tert-butoxy)-2-(2-(3-chlorophenyl)-8-(8-fluoro-5-methylchroman-6-yl)-6-methylimidazo[1,2-a]pyridin-7-yl)acetate In a microwave vial, 2-methylprop-1-ene (g) was condensed into a stirring solution of perchloric acid (10 μl, 0.12 mmol) and (2S)-ethyl 2-(2-(3-chlorophenyl)-8-(8-fluoro-5-methylchroman-6-yl)-6-methylimidazo[1,2-a]pyridin-7-yl)-2-hydroxyacetate (20 mg, 0.039 mmol) in CH2Cl2 (0.8 ml) at −35° C. for 5 min. The solution was sealed and allowed to stir at rt. LCMS showed mostly starting material remained. After 1 h an additional drop of perchloric acid was added and the reaction was allowed to stir overnight at rt. LCMS showed mostly starting material remained. The mixture was diluted with EtOAc and washed with sat aq NaHCO3, and sat aq NaCl. The organic phase was dried over Na2SO4, filtered and concentrated. The residue was taken up in 2 ml, of tbutylacetate in a sealed microwave vial. Several drops of perchloric acid was added. LCMS after 5 min showed nearly 50% conversion. After 30 min no additional change was observed by LCMS. The mixture was diluted with EtOAc and washed with sat aq NaHCO3, and sat aq NaCl. The organic phase was dried over Na2SO4, filtered, concentrated adsorbing onto Celite and finally purified on silica gel (Biotage, EtOAc/hexanes gradient, fraction collection at λ=254 nm) to give the expected product (2S)-ethyl 2-(tert-butoxy)-2-(2-(3-chlorophenyl)-8-(8-fluoro-5-methylchroman-6-yl)-6-methylimidazo[1,2-a]pyridin-7-yl)acetate (10 mg, 0.018 mmol, 45% yield). LC-MS retention time: 1.27 min; m/z (MH+): 565. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

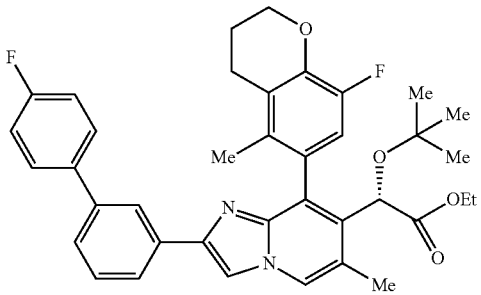 [SMILES: CCOC(=O)[C@@H](OC(C)(C)C)c1c(C)cn2cc(-c3cccc(-c4ccc(F)cc4)c3)nc2c1-c1cc(F)c2c(c1C)CCCO2]

(2S)-Ethyl 2-(tert-butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetate (4-Fluorophenyl)boronic acid (12 mg, 0.088 mmol), (2S)-ethyl 2-(tert-butoxy)-2-(2-(3-chlorophenyl)-8-(8-fluoro-5-methylchroman-6-yl)-6-methylimidazo[1,2-a]pyridin-7-yl) acetate (10 mg, 0.018 mmol), sodium 6-(dicyclohexylphosphino)-2',6'-dimethoxy-[1,1'-biphenyl]-3-sulfonate (5.0 mg, 11 μmol), Pd(OAc)$_2$ (1 mg, 5 μmol), cesium carbonate (20 mg, 0.062 mmol) were combined, degassed and taken up in DMF (644 μl) and water (64.4 μl) at rt. The reaction mixture was heated at 80° C. and allowed to stir for 1 h. The reaction was then concentrated, adsorbed onto Celite and was purified on silica gel (Biotage, EtOAc/hexanes gradient, fraction collection at λ=254 nm) to give the expected product (2S)-ethyl 2-(tert-butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetate (10 mg, 0.016 mmol, 90% yield). LC-MS retention time: 1.34 min; m/z (MH+): 625. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

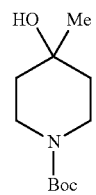

tert-Butyl 4-hydroxy-4-methylpiperidine-1-carboxylate

Methylmagnesium bromide (41.8 mL, 125 mmol) was added to a stirring solution of tert-butyl 4-oxopiperidine-1-carboxylate (25.0 g, 125 mmol) in diethyl ether (250 mL) at −30° C. The white slurry was allowed to warm to rt and stir for 2 h. The reaction was placed in a rt water bath. Water (100 mL) was then added drop wise, followed by saturated NH$_4$Cl (100 mL) and the ether layer was separated. The aqueous phase was further extracted with ether (200 mL) and the combined organic phase was washed with brine (50 mL), dried (Na$_2$SO$_4$), filtered and concentrated to afford tert-butyl 4-hydroxy-4-methylpiperidine-1-carboxylate (25.0 g, 116 mmol, 93% yield) as colorless oil. $^1$H NMR (500 MHz, CDCl$_3$) δ 3.74-3.67 (m, 2H), 3.28-3.21 (m, 2H), 1.57-1.53 (m, 4H), 1.46 (s, 9H), 1.27 (s, 3H).

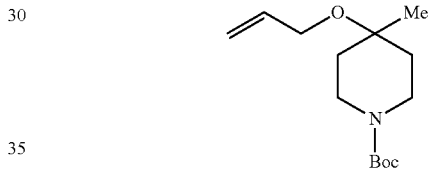

tert-Butyl 4-(allyloxy)-4-methylpiperidine-1-carboxylate

To a mixture of tert-butyl 4-hydroxy-4-methylpiperidine-1-carboxylate (6.10 g, 28.3 mmol) in DMF (20 mL) at 0° C. was added NaH (2.27 g, 56.7 mmol) and the mixture was then stirred at rt for 30 min. Then allyl bromide (12.3 mL, 142 mmol) was slowly added and the mixture was stirred at rt for 3 h. The reaction was then cooled to 0° C., quenched with sat aq NH$_4$Cl, extracted with ether and the organic was then dried over Na$_2$SO$_4$, filtered and concentrated to obtain a colorless oil, which was then purified by biotage, eluting with EtOAc/hexane gradient to isolate the expected product tert-butyl 4-(allyloxy)-4-methylpiperidine-1-carboxylate (6.2 g, 24 mmol, 86% yield) consistent by NMR. $^1$H NMR (400 MHz, CDCl$_3$) δ 5.99-5.87 (m, 1H), 5.31 (dd, J=17.1, 1.8 Hz, 1H), 5.14 (dd, J=10.4, 1.4 Hz, 1H), 3.89 (d, J=5.3 Hz, 2H), 3.72 (d, J=13.3 Hz, 2H), 3.21-3.12 (m, 2H), 1.77 (d, J=12.8 Hz, 2H), 1.46 (s, 9H), 1.43 (d, J=13.6 Hz, 2H), 1.20 (s, 3H).

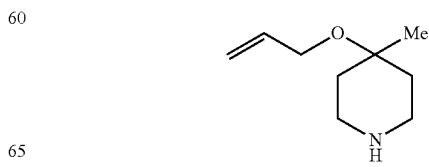

4-(Allyloxy)-4-methylpiperidine hydrochloride

A mixture of tert-butyl 4-(allyloxy)-4-methylpiperidine-1-carboxylate (3.10 g, 12.1 mmol) and 4N HCl/dioxane (15 mL, 60 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, METHANOL-d4) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

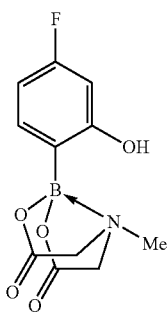 [SMILES: C[N+]12CC(=O)O[B-]1(c1ccc(F)cc1O)OC(=O)C2]

2-(4-Fluoro-2-hydroxyphenyl)-6-methyl-1,3,6,2-dioxazaborocane-4,8-dione 2,2'-(Methylazanediyl)diacetic acid (0.566 g, 3.85 mmol) and (4-fluoro-2-hydroxyphenyl)boronic acid (0.50 g, 3.2 mmol) were taken up in toluene (4.3 ml) and DMSO (2.2 ml) at rt. The reaction mixture was equipped with Dean-Stark trap and the mixture was stirred at 125° C. for 3 h. The reaction was allowed to cool to rt and was then taken up in EtOAc and water. The organic layer was separated, concentrated, adsorbed onto Celite and was purified on silica gel (Biotage, EtOAc/hexanes gradient and flushed with acetone at the end, TLCs were visualized with permanganate stain). The fractions containing the expected product were concentrated to give 760 mg of the title compound as a white solid. $^1$H NMR (500 MHz, DMSO-d6) δ 10.09 (s, 1H), 7.38 (t, J=8.0 Hz, 1H), 6.60 (td, J=8.6, 2.4 Hz, 1H), 6.53 (dd, J=11.2, 2.4 Hz, 1H), 4.33 (d, J=17.0 Hz, 2H), 4.02 (d, J=17.0 Hz, 2H), 2.63 (s, 3H).

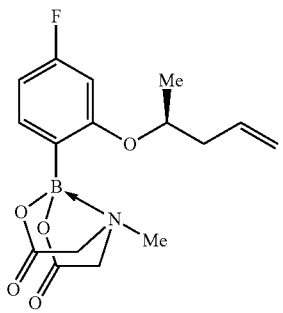 [SMILES: C=CC[C@H](C)Oc1cc(F)ccc1[B-]12OC(=O)C[N+]1(C)CC(=O)O2]

(S)-2-(4-Fluoro-2-(pent-4-en-2-yl oxy)phenyl)-6-methyl-1,3,6,2-dioxazaborocane-4,8-dione (E)-Diethyl diazene-1,2-dicarboxylate (0.54 ml, 3.4 mmol) was added drop wise to triphenylphosphine (0.90 g, 3.4 mmol) in THF (29 ml) at 0° C. The solution was allowed to stir for 1 h. (R)-Pent-4-en-2-ol (0.351 ml, 3.42 mmol) was added the mixture and it was allowed to stir for 15 min. Then, (4r,8r)-8-(4-fluoro-2-hydroxyphenyl)-4-methyl-2,6-dioxohexahydro-[1,3,2]oxazaborolo[2,3-b][1,3,2]oxazaborol-4-ium-8-uide (0.76 g, 2.9 mmol) was added and the mixture was allowed to warm to rt and stir overnight. The reaction was concentrated, adsorbed onto Celite and was purified on silica gel (Biotage, EtOAc/acetone gradient, fraction collection at λ=254 nm) to give the expected product (S)-8-(4-fluoro-2-(pent-4-en-2-yloxy)phenyl)-4-methyl-2,6-dioxohexahydro-[1,3,2]oxazaborolo[2,3-b][1,3,2]oxazaborol-4-ium-8-uide (343 mg, 1.02 mmol, 36% yield). $^1$H NMR (500 MHz, DMSO-d6) δ 7.48-7.42 (m, 1H), 6.95-6.90 (m, 1H), 6.75-6.69 (m, 1H), 5.88-5.77 (m, 1H), 5.16-5.03 (m, 2H), 4.69-4.61 (m, 1H), 4.43-4.31 (m, 2H), 4.01-3.92 (m, 2H), 2.59 (s, 3H), 2.44-2.38 (m, 1H), 2.30-2.23 (m, 1H), 1.18-1.16 (m, 3H).

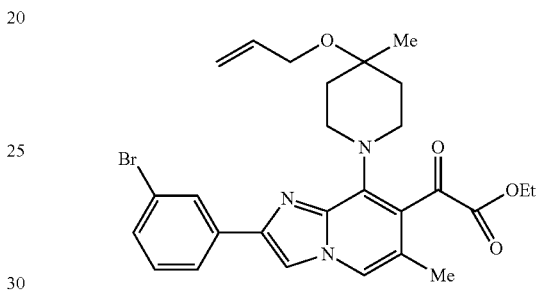

Ethyl 2-(8-(4-(allyloxy)-4-methylpiperidin-1-yl)-2-(3-bromophenyl)-6-methylimidazo[1,2-a]pyridin-7-yl)-2-oxoacetate 4-(Allyloxy)-4-methylpiperidine (167 mg, 1.07 mmol) was added to a stirring solution of DIEA (187 µl, 1.07 mmol) and ethyl 2-(8-bromo-2-(3-bromophenyl)-6-methylimidazo[1,2-a]pyridin-7-yl)-2-oxoacetate (100 mg, 0.215 mmol) in acetonitrile (4.3 ml) at rt. The reaction was allowed to stir for 7 days. The reaction was then concentrated, adsorbed onto Celite and was purified on silica gel (Biotage, 40 g column EtOAc/hexanes gradient, fraction collection at λ=254 nm) to give the expected product ethyl 24844-(allyloxy)-4-methylpiperidin-1-yl)-2-(3-bromophenyl)-6-methylimidazo[1,2-a]pyridin-7-yl)-2-oxoacetate (53 mg, 0.098 mmol, 46% yield). $^1$H NMR (500 MHz, DMSO-d6) δ 8.56 (s, 1H), 8.30 (d, J=1.3 Hz, 1H), 8.22-8.18 (m, 1H), 8.01-7.97 (m, 1H), 7.56-7.52 (m, 1H), 7.43 (s, 1H), 6.06-5.97 (m, 1H), 5.51-5.45 (m, 1H), 5.23-5.18 (m, 1H), 4.28 (d, J=7.1 Hz, 2H), 3.95 (d, J=4.7 Hz, 2H), 3.85-3.75 (m, 2H), 2.90-2.81 (m, 2H), 2.21 (d, J=0.9 Hz, 3H), 1.87-1.79 (m, 2H), 1.60-1.52 (m, 2H), 1.29 (t, J=7.1 Hz, 3H), 1.22 (s, 3H). LC-MS retention time: 1.64 min; m/z (MH+): 542. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

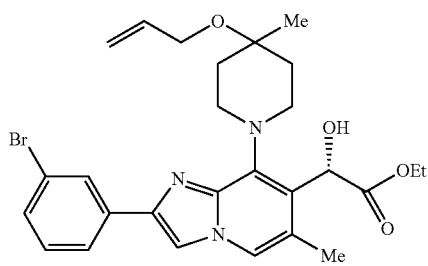 [SMILES: C=CCOC1(C)CCN(c2c([C@H](O)C(=O)OCC)c(C)cn3cc(-c4cccc(Br)c4)nc23)CC1]

(S)-Ethyl 2-(8-(4-(allyloxy)-4-methylpiperidin-1-yl)-2-(3-bromophenyl)-6-methylimidazo[1,2-a]pyridin-7-yl)-2-hydroxyacetate (R)-1-Methyl-3,3-diphenylhexahydropyrrolo[1,2-c][1,3,2]oxazaborole (1M in toluene) (52 µl, 0.052 mmol) was added to a solution of ethyl 2-(8-(4-(allyloxy)-4-methylpiperidin-1-yl)-2-(3-bromophenyl)-6-methylimidazo[1,2-a]pyridin-7-yl)-2-oxoacetate (70 mg, 0.13 mmol) in Toluene (3.7 ml) at rt. The mixture was cooled to −35° C. and treated with catecholborane (50% in toluene) (44 µl, 0.18 mmol) drop wise. The reaction was stirred for 2 h while maintaining temperatures between −35° C. and −15° C. The reaction was quenched with 2M aq $Na_2CO_3$ at −20° C. and the mixture was allowed to stir for 15 min. The mixture was then diluted with EtOAc and washed with sat aq $Na_2CO_3$, and sat aq NaCl. The organic phase was concentrated, adsorbed onto Celite and was purified on silica gel (Biotage, EtOAc/hexanes gradient, fraction collection at λ=254 nm) to give the expected product (S)-ethyl 2-(8-(4-(allyloxy)-4-methylpiperidin-1-yl)-2-(3-bromophenyl)-6-methylimidazo[1,2-a]pyridin-7-yl)-2-hydroxyacetate (53 mg, 0.098 mmol, 75% yield). $^1$H NMR (500 MHz, DMSO-d6) δ 8.78 (s, 1H), 8.39-8.33 (m, 1H), 8.23-8.16 (m, 2H), 7.99-7.93 (m, 1H), 7.54-7.47 (m, 1H), 7.44-7.33 (m, 1H), 6.76-6.67 (m, 1H), 6.62-6.55 (m, 1H), 6.23-6.14 (m, 1H), 6.13-6.02 (m, 1H), 5.62-5.49 (m, 1H), 5.30-5.19 (m, 1H), 4.35-4.23 (m, 1H), 4.22-4.12 (m, 1H), 4.02-3.93 (m, 2H), 2.78-2.66 (m, 1H), 2.27 (d, J=0.8 Hz, 3H), 1.88-1.41 (m, 4H), 1.24-1.16 (m, 3H), 1.15-1.11 (m, 3H). LC-MS retention time: 1.28 min; m/z (MH+): 544. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

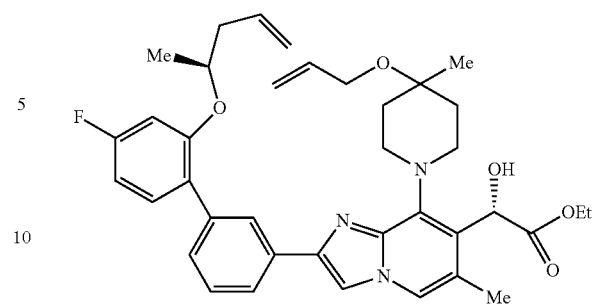

(S)-Ethyl 2-(8-(4-(allyloxy)-4-methylpiperidin-1-yl)-2-(4'-fluoro-2-((S)-pent-4-en-2-yloxy)-[1,1'-biphenyl]-3-yl)-6-methylimidazo[1,2-a]pyridin-7-yl)-2-hydroxyacetate (S)-Ethyl 2-(8-(4-(allyloxy)-4-methylpiperidin-1-yl)-2-(3-bromophenyl)-6-methylimidazo[1,2-a]pyridin-7-yl)-2-hydroxyacetate (170 mg, 0.313 mmol), (S)-8-(4-(fluoro-2-(pent-4-en-2-yloxy)phenyl)-4-methyl-2,6-dioxohexahydro-[1,3,2]oxazaborolo[2,3-b][1,3,2]oxazaborol-4-ium-8-uide (116 mg, 0.345 mmol), $Pd(OAc)_2$ (7.0 mg, 0.031 mmol), dicyclohexyl(2',6'-dimethoxy-[1,1'-biphenyl]-2-yl)phosphine (26 mg, 0.063 mmol), tripotassium phosphate (499 mg, 2.35 mmol)(crushed) were combined dry, degassed, backfilled with N2, and taken up in Dioxane (5.2 ml) and water (1.0 ml) at rt. The reaction was heated at 80° C. for 1 h. The reaction was then concentrated, adsorbed onto Celite and was purified on silica gel (Biotage, EtOAc/hexanes gradient, fraction collection at λ=254 nm) to give to give the expected product (S)-ethyl 2-(8-(4-(allyloxy)-4-methylpiperidin-1-yl)-2-(4'-fluoro-2'-((S)-pent-4-en-2-yloxy)-[1,1'-biphenyl]-3-yl)-6-methylimidazo[1,2-a]pyridin-7-yl)-2-hydroxyacetate (170 mg, 0.265 mmol, 85% yield). LC-MS retention time: 1.41 min; m/z (MH+): 642. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2/O 90% acetonitrile/0.1% trifluoroacetic acid. MS data was determined using a Micromass Platform for LC in electrospray mode.

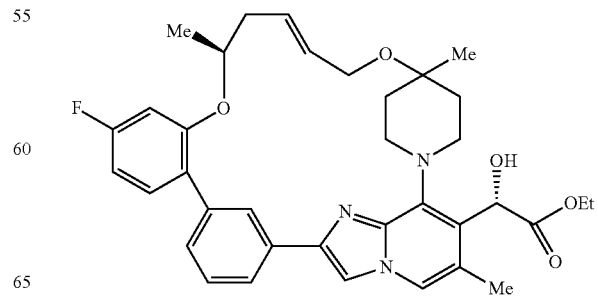

Ethyl (2S)-[(22S,24E)-18-fluoro-4,22,28-trimethyl-21,27-dioxa-1,6,8-triazahexacyclo[26.2.2.16,9.110,14.02,7.015,20]tetratriaconta-2,4,7,9(34),10(33),11,13,15,17,19,24-undecaen-3-yl](hydroxy)acetate Hoveyda-Grubbs catalyst $2^{nd}$ generation (25 mg, 0.040 mmol) and tosic acid (50 mg, 0.27 mmol) was added to a stirring degassed and backfilled with $N_2$ (3x) solution of (S)-ethyl 2-(8-(4-(allyloxy)-4-methylpiperidin-1-yl)-2-(4'-fluoro-2'-((S)-pent-4-en-2-yloxy)-[1,1'-biphenyl]-3-yl)-6-methylimidazo[1,2-a]pyridin-7-yl)-2-hydroxyacetate (170 mg, 0.265 mmol) in DCE (13.2 ml) at rt. The reaction was allowed to stir at 70° C. for 1 h. The reaction was then concentrated, adsorbed onto Celite and was purified on silica gel (Biotage, EtOAc/hexanes gradient, fraction collection at λ=254 nm) to give the expected product (110 mg, 0.179 mmol, 68% yield). LC-MS retention time: 1.35 min; m/z (MH+): 614. LC data was recorded on a Shimadzu LC-10AS liquid chromatograph equipped with a Waters Aquity BEH C18 2.1x50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% $H_2O$/90% acetonitrile/0.1% trifluoroacetic acid. MS data was determined using a Micromass Platform for LC in electrospray mode.

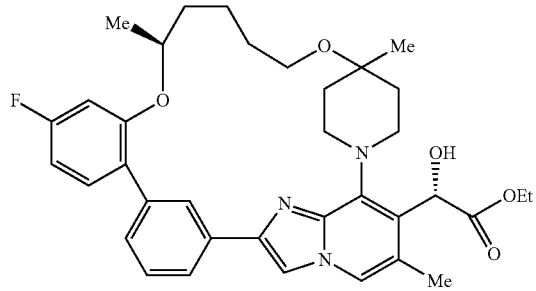 [SMILES: CCOC(=O)[C@@H](O)c1c(C)cn2cc3nc2c1N1CCC(C)(CC1)OCCCC[C@H](C)Oc1cc(F)ccc1-c1cccc-3c1]

Ethyl (2S)-[(22S)-18-fluoro-4,22,28-trimethyl-21,27-dioxa-1,6,8-triazahexacyclo[26.2.2.16,9.110,14.02,7.015,20]tetratriaconta-2,4,7,9 (34),10(33),11,13,15,17,19-decaen-3-yl](hydroxy)acetate NaBH$_4$ (18 mg, 0.49 mmol) was added to a stirring solution of ethyl (2S)-[(22S,24E)-18-fluoro-4,22,28-trimethyl-21,27-dioxa-1,6,8 triazahexacyclo[26.2.2.16,9.110,14.02,7.015,20]tetratriaconta-2,4,7,9(34),10(33),11,13,15,17,19,24-undecaen-3-yl](hydroxy)acetate (100 mg, 0.163 mmol) and Grubbs $2^{nd}$ generation catalyst (14 mg, 0.016 mmol) in dichloromethane (14 ml) and EtOH (1.4 ml) at rt. The reaction was allowed to stir for 2 h. Additional NaBH$_4$ (18 mg, 0.49 mmol) was added and the reaction was allowed to stir for another 1 h. Then another aliquot of NaBH$_4$ (18 mg, 0.49 mmol) was added and the reaction was allowed to stir for a final 1 h. The mixture was then diluted with dichloromethane and washed with sat NaHCO$_3$, and sat NaCl. The organic phase was concentrated azeotroping with toluene 2x. The crude residue was taken up in DCM and adsorbed onto Celite and was purified on silica gel (Biotage, EtOAc/hexanes gradient, fraction collection at λ=254 nm) to give the reduced product (91 mg, 0.15 mmol, 91% yield). $^1$H NMR (500 MHz, DMSO-d6) δ 8.43-8.37 (m, 1H), 8.35-8.31 (m, 1H), 8.17-8.14 (m, J=1.1 Hz, 1H), 7.82-7.78 (m, 1H), 7.46-7.41 (m, 1H), 7.30-7.25 (m, 1H), 7.20-7.16 (m, 1H), 7.12-7.06 (m, 1H), 6.84-6.79 (m, 1H), 5.92-5.81 (m, 1H), 5.68-5.62 (m, 1H), 4.73-4.66 (m, 1H), 4.60-4.36 (m, 1H), 4.21-4.01 (m, 2H), 3.46-3.36 (m, 2H), 2.97-2.89 (m, 1H), 2.28-2.22 (m, 3H), 2.03-1.93 (m, 1H), 1.78-1.38 (m, 9H), 1.19-1.06 (m, 10H). LC-MS retention time: 1.44 min; m/z (MH+): 616. LC data was recorded on a Shimadzu LC-10AS liquid chromatograph equipped with a Waters Aquity BEH C18 2.1x50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

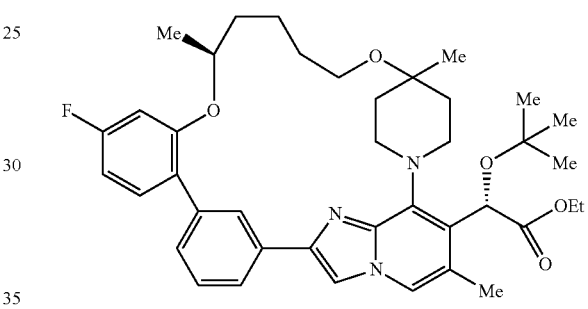

Ethyl (2S)-tert-butoxy[(22S)-18-fluoro-4,22,28-trimethyl-21,27-dioxa-1,6,8-triazahexacyclo[26.2.2.16, 9.110,14.02,7.015,20]tetratriaconta-2,4,7,9(34),10 (33),11,13,15,17,19-decaen-3-yl]acetate 2-Bromo-2-methylpropane (45 μl, 0.39 mmol) was added to a stirring slurry of ethyl (2S)-[(22S)-18-fluoro-4,22,28-trimethyl-21,27-dioxa-1,6,8-triazahexacyclo[26.2.2.16, 9.110,14.02,7.015,20]tetratriaconta-2,4,7,9(34),10(33),11, 13,15,17,19-decaen-3-yl](hydroxy)acetate (40 mg, 0.065 mmol) and silver oxide (45 mg, 0.20 mmol) in dichloromethane (1.3 ml) and cyclohexane (1.3 ml) at rt under $N_2$ balloon. The reaction mixture was allowed to stir 4 h. Then an additional aliquot of reagents: silver oxide (45 mg, 0.20 mmol) and 2-bromo-2-methylpropane (45 μl, 0.39 mmol) were added and the reaction was allowed to stir for 3 days at 35° C. The reaction was concentrated, adsorbed onto Celite and was purified on silica gel (Biotage, EtOAc/hexanes gradient, fraction collection at λ=254 nm) to give the expected product (5.0 mg, 7.0 μmol, 12% yield). LC-MS retention time: 1.60 min; m/z (MH+): 672. LC data was recorded on a Shimadzu LC-10AS liquid chromatograph equipped with a Waters Aquity BEH C18 2.1x50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

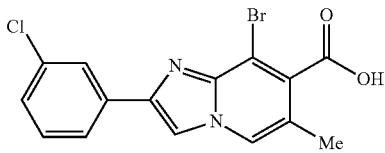 [SMILES: Cc1cn2cc(-c3cccc(Cl)c3)nc2c(Br)c1C(=O)O]

8-Bromo-2-(3-chlorophenyl)-6-methylimidazo[1,2-a]pyridine-7-carboxylic acid

Aqueous 2M LiOH (70 ml, 140 mmol) was added to a stirring solution of methyl 8-bromo-2-(3-chlorophenyl)-6-methylimidazo[1,2-a]pyridine-7-carboxylate (13.3 g, 35.0 mmol) in MeOH (100 ml) and THF (100 ml) at rt. The reaction was equipped with a vigreux condenser and was heated to 80° C. and allowed to stir for 7 h. The reaction mixture was cooled to rt and allowed to continue to stir at this temp overnight. The reaction mixture was then concentrated to an aq mixture, diluted with EtOAc (100 mL) and washed with 1M HCl (100 mL). The aq layer was extracted with EtOAc (2×50 mL). The combined organic extracts were washed with water, dried over $Na_2SO_4$, filtered and concentrated to give the expected product 8-bromo-2-(3-chlorophenyl)-6-methylimidazo[1,2-a]pyridine-7-carboxylic acid (10.2 g, 27.9 mmol, 80% yield). $^1$H NMR (500 MHz, DMSO-d6) δ 14.06 (br. s., 1H), 8.60 (s, 1H), 8.51-8.42 (m, 1H), 8.04 (s, 1H), 7.96 (d, J=7.9 Hz, 1H), 7.49 (t, J=7.9 Hz, 1H), 7.45-7.36 (m, 1H), 2.28 (s, 3H). LC-MS retention time: 0.89 min; m/z (MH+): 366. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

(S)-Methyl 2-(8-bromo-2-(3-chlorophenyl)-6-methylimidazo[1,2-a]pyridin-7-yl)-2-hydroxyacetate Step 1: DIEA (18.6 ml, 107 mmol) was added to a stirring solution of 8-bromo-2-(3-chlorophenyl)-6-methylimidazo[1,2-a]pyridine-7-carboxylic acid (13 g, 36 mmol), and HATU (16.2 g, 42.7 mmol) in DCM (356 ml) at rt. After 10 min of stirring the heavy white ppt slowly dissolved. Next, 1-(cyanomethyl)tetrahydro-1H-thiophen-1-ium bromide (8.14 g, 39.1 mmol) was added in a single aliquot. LCMS after 2 h reveals approximately 50% conversion. Additional HATU (16.2 g, 42.7 mmol) and 1-(cyanomethyl)tetrahydro-1H-thiophen-1-ium bromide (8.14 g, 39.1 mmol) were added and the mixture was allowed to continue to stir overnight. LCMS shows roughly a 3:1 mixture of desired product and activated ester. The reaction mixture was diluted with sat aq $NH_4Cl$. The layers were separated and the aq layer was extracted with DCM (2×90 mL) and concentrated to give an orange solid. This solid was adsorbed onto Celite and purified on silica gel (Biotage) eluting first with a 0-100% EtOAc in hexanes gradient over 12 CV to remove all non-polar biproducts. This eluant was followed by a eluting with a 0-10% MeOH in DCM gradient over 12 CV to give both activated ester 3H-[1,2,3]triazolo[4,5-b]pyridin-3-yl 8-bromo-2-(3-chlorophenyl)-6-methylimidazo[1,2-a]pyridine-7-carboxylate (6.3 g, 9.8 mmol, 28% yield), which was resubjected to reaction conditions, as well as desired 3-[8-bromo-2-(3-chlorophenyl)-6-methylimidazo[1,2-a]pyridin-7-yl]-3-oxo-2-(1λ$^4$-thiolan-1-ylidene)propanenitrile (7.8 g, 16 mmol, 46% yield). LC-MS retention time: 0.95 min; m/z (MH+): 476. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: A suspension of 3-[8-bromo-2-(3-chlorophenyl)-6-methylimidazo[1,2-a]pyridin-7-yl]-3-oxo-2-(1λ$^4$-thiolan-1-ylidene)propanenitrile (3.5 g, 7.4 mmol) and Oxone (13.6 g, 22.1 mmol) in anhydrous MeOH (150 ml) and water (15 ml) was stirred exposed to air for 6 h. The reaction mixture was filtered rinsing with DCM until the solids were colorless. The filtrate was neutralized with the addition of sat aq NaHCO3 with vigorous stirring in an Erlenmyer flask. The aq mixture was then concentrated to remove organics. The aq mixture was extracted with DCM (2×50 mL). The combined organic extracts were washed with water, dried over $Na_2SO_4$, filtered and concentrated to give an orange solid. This solid was adsorbed onto Celite and then purified on silica gel eluting with a 0-75% EtOAc in hexanes gradient over 12 CV to give methyl 2-(8-bromo-2-(3-chlorophenyl)-6-methylimidazo[1,2-a]pyridin-7-yl)-2-oxoacetate (2.0 g, 4.9 mmol, 67% yield) as a yellow solid. LC-MS retention time: 1.31 min; m/z (MH+): 409. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 3: (R)-1-Methyl-3,3-diphenylhexahydropyrrolo[1,2-c][1,3,2]oxazaborole (1M in toluene) (1.9 ml, 1.9 mmol) was added to a solution of methyl 2-(8-bromo-2-(3-chlorophenyl)-6-methylimidazo[1,2-a]pyridin-7-yl)-2-oxoacetate (1.9 g, 4.7 mmol) in Toluene (133 ml) at rt. The mixture was cooled to −35° C. and treated with catecholborane (50% in toluene) (1.48 ml, 6.06 mmol) drop wise. The reaction mixture was allowed to stir 0.5 h with warming from −35° C. to −15° C. LCMS shows full conversion with the yellow hue no longer visible signifying the consumption of the alpha keto ester which is bright yellow in color. The reaction mixture was quenched with 2M Na$_2$CO$_3$ at −20° C. and allowed to stir for 15 min. The neutralized mixture was diluted with EtOAc and washed with sat Na$_2$CO$_3$, and sat NaCl. The organic phase was dried over Na$_2$SO$_4$, filtered, concentrated and adsorbed onto Celite and was purified on silica gel (Biotage, EtOAc/hexanes gradient, fraction collection at λ=254 nm) to give to the expected product (S)-methyl 2-(8-bromo-2-(3-chlorophenyl)-6-methylimidazo[1,2-a]pyridin-7-yl)-2-hydroxyacetate (743 mg, 1.81 mmol, 39% yield). $^1$H NMR (500 MHz, DMSO-d6) δ 8.53 (s, 1H), 8.35 (d, J=1.1 Hz, 1H), 8.03 (t, J=1.8 Hz, 1H), 7.95 (dt, J=7.8, 1.2 Hz, 1H), 7.52-7.45 (m, 1H), 7.40 (ddd, J=8.0, 2.1, 1.1 Hz, 1H), 6.46 (d, J=4.9 Hz, 1H), 5.85 (d, J=4.9 Hz, 1H), 3.66 (s, 3H), 2.26 (d, J=0.9 Hz, 3H)LC-MS retention time: 1.00 min; m/z (MH+): 411. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

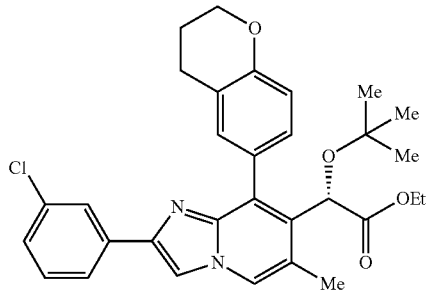 [SMILES: CCOC(=O)[C@@H](OC(C)(C)C)c1c(C)cn2cc(-c3cccc(Cl)c3)nc2c1-c1ccc2c(c1)CCCO2]

(S)-Methyl 2-(tert-butoxy)-2-(2-(3-chlorophenyl)-8-(chroman-6-yl)-6-methylimidazo[1,2-a]pyridin-7-yl)acetate Step 1: Perchloric acid (0.41 mL, 4.8 mmol) was added to a sealed stirring solution of (S)-methyl 2-(8-bromo-2-(3-chlorophenyl)-6-methylimidazo[1,2-a]pyridin-7-yl)-2-hydroxyacetate (650 mg, 1.59 mmol) in tBuOAc (50 mL) at rt. Upon addition of the acid, ppt formation was observed. The reaction mixture was allowed to stir for 1 h. The mixture was then diluted with EtOAc and washed with sat NaHCO$_3$, and sat NaCl. The organic phase was dried over Na$_2$SO$_4$, filtered, concentrated, adsorbed onto Celite and purified on silica gel (Biotage, EtOAc/hexanes gradient, fraction collection at λ=254 nm) to give recovered starting material (S)-methyl 2-(8-bromo-2-(3-chlorophenyl)-6-methylimidazo[1,2-a]pyridin-7-yl)-2-hydroxyacetate (580 mg, 1.416 mmol, 89% yield) as well as the desired t-Butyl ester product (S)-methyl 2-(8-bromo-2-(3-chlorophenyl)-6-methylimidazo[1,2-a]pyridin-7-yl)-2-(tert-butoxy)acetate (68 mg, 0.15 mmol, 9% yield). LC-MS retention time: 1.29 min; m/z (MH+): 467. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2: (S)-Methyl 2-(8-bromo-2-(3-chlorophenyl)-6-methylimidazo[1,2-a]pyridin-7-yl)-2-(tert-butoxy)acetate (80 mg, 0.17 mmol) was then combined with 2-(chroman-6-yl)-4,4,5,5-tetramethyl-1,3,2-dioxaborolane (63 mg, 0.24 mmol), cesium carbonate (112 mg, 0.344 mmol), PdCl$_2$(dppf) (12 mg, 0.017 mmol) in DMF (3.1 mL) and Water (0.31 mL) at rt. The mixture was degassed, backfilled with N$_2$ and warmed to 60° C. The reaction mixture was allowed to stir at this temp for 1 h. The reaction mixture was then concentrated, adsorbed onto Celite and purified on silica gel (Biotage, EtOAc/hexanes gradient, fraction collection at λ=254 nm) to give the expected product (S)-methyl 2-(tert-butoxy)-2-(2-(3-chlorophenyl)-8-(chroman-6-yl)-6-methylimidazo[1,2-a]pyridin-7-yl)acetate (46 mg, 0.089 mmol, 52% yield). $^1$H NMR (500 MHz, CDCl$_3$) δ 7.94-7.82 (m, 2H), 7.82-7.69 (m, 2H), 7.48-7.37 (m, 1H), 7.31-7.19 (m, 3H), 6.95 (m, 1H), 5.38 (br. s., 1H), 4.28 (m, 2H), 3.79 (s, 3H), 2.81 (m, 2H), 2.36 (s, 3H), 2.16-2.04 (m, 2H), 1.04-0.90 (m, 9H). LC-MS retention time: 1.20 min; m/z (MH+): 520. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H$_2$O/90% acetonitrile/0.1% trifluoroacetic acid. MS data was determined using a Micromass Platform for LC in electrospray mode.

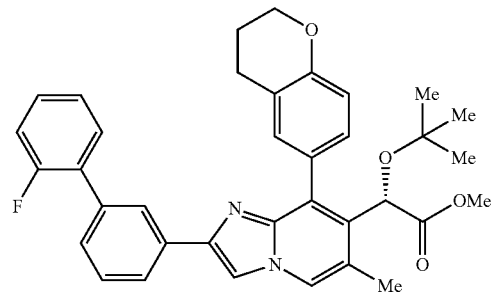 [SMILES: COC(=O)[C@@H](OC(C)(C)C)c1c(C)cn2cc(-c3cccc(-c4ccccc4F)c3)nc2c1-c1ccc2c(c1)CCCO2]

(S)-Methyl 2-(tert-butoxy)-2-(8-(chroman-6-yl)-2-(2'-fluoro-[1,1'-biphenyl]-3-yl)-6-methylimidazo[1,2-a]pyridin-7-yl)acetate (S)-Methyl 2-(tert-butoxy)-2-(2-(3-chlorophenyl)-8-(chroman-6-yl)-6-methylimidazo[1,2-a]pyridin-7-yl)acetate (45 mg, 0.087 mmol), (2-fluorophenyl)boronic acid (24 mg, 0.17 mmol), Cs$_2$CO$_3$ (57 mg, 0.17 mmol), PdOAc$_2$ (1.9 mg, 8.7 μmol), and 2-dicyclohexylphosphino-2',6'-dimethoxybiphenyl (SPhos) (7.1 mg, 0.017 mmol) were combined in a sealed reaction vessel. The dry mixture was evacuated and charged with N$_2$ (3×). The solids were then taken up in a mixture of DMF (2 mL)/water (0.2 mL) and heated to 80° C. The mixture was stirred at this temperature for 2 h. LCMS shows a mixture of des-Cl, starting material and desired product. The mixture was diluted with EtOAc and washed with sat aq NH4Cl. The layers were separated and the aq layer was extracted with EtOAc (2×10 mL). The combined organic extracts were washed with brine, dried over Na$_2$SO$_4$, filtered and concentrated to give a yellow oil. This oil was adsorbed onto Celite, and then purified on silica gel eluting with a 0-75% EtOAc in hexanes gradient over 12 CV to give (S)-methyl 2-(tert-butoxy)-2-(8-(chroman-6-yl)-2-(2'-fluoro-[1,1'-biphenyl]-3-yl)-6-methylimidazo[1,2-a]pyridin-7-yl)acetate (25 mg, 0.043 mmol, 50% yield) as a yellow oil. $^1$H NMR (500 MHz, CDCl$_3$) δ 8.02-7.76 (m, 3H), 7.54-7.41 (m, 3H), 7.39-7.30 (m, 2H), 7.29-7.11 (m, 4H), 6.92 (d, J=13.7 Hz, 1H), 5.38 (m, 1H), 4.32-4.24 (m, 2H), 3.79 (m, 3H), 2.81 (m, 2H), 2.36 (br. s., 3H), 2.12-2.05 (m, 3H), 0.99-0.94 (m, 9H). LC-MS retention time: 1.29 min; m/z (MH+): 579. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

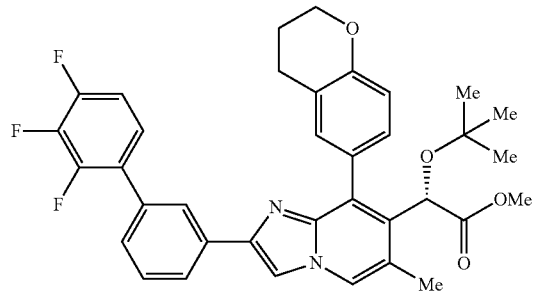 [SMILES: COC(=O)[C@@H](OC(C)(C)C)c1c(C)cn2cc(-c3cccc(-c4ccc(F)c(F)c4F)c3)nc2c1-c1ccc2c(c1)CCCO2]

(S)-Methyl 2-(tert-butoxy)-2-(8-(chroman-6-yl)-6-methyl-2-(2',3',4'-trifluoro-[1,1'-biphenyl]-3-yl)imidazo[1,2-a]pyridin-7-yl)acetate (S)-Methyl 2-(tert-butoxy)-2-(2-(3-chlorophenyl)-8-(chroman-6-yl)-6-methylimidazo[1,2-a]pyridin-7-yl)acetate (20 mg, 0.039 mmol), (2,3,4-trifluorophenyl)boronic acid (14 mg, 0.077 mmol), PdOAc$_2$ (0.1 equiv),dicyclohexyl(2',6'-diisopropoxy-[1,1'-biphenyl]-2-yl)phosphine (3.6 mg, 7.7 μmol), cesium carbonate (38 mg, 0.12 mmol) were combined, degassed, backfilled with N$_2$, and taken up in DMF (7 mL) and water (0.7 mL) at rt. The reaction was heated to 80° C. and stirred at this temp for 1 h. The mixture was concentrated, adsorbed onto Celite and purified on silica gel eluting with a 0-100% EtOA in hexanes mixture over 12 CV to give (S)-methyl 2-(tert-butoxy)-2-(8-(chroman-6-yl)-6-methyl-2-(2',3',4'-trifluoro-[1,1'-biphenyl]-3-yl)imidazo[1,2-a]pyridin-7-yl)acetate (20 mg, 0.033 mmol, 84% yield) as a off-white solid. $^1$H NMR (500 MHz, CDCl$_3$) δ 7.99-7.81 (m, 4H), 7.50-7.34 (m, 3H), 7.25-7.15 (m, 2H), 7.03 (d, J=8.8 Hz, 1H), 6.99-6.82 (m, 1H), 5.38 (br. s., 1H), 4.27 (t, J=5.0 Hz, 2H), 3.79 (s, 3H), 2.81 (m, 2H), 2.37 (br. s., 3H), 2.14-1.98 (m, 2H), 1.68 (br. s., 2H), 1.02-0.90 (m, 9H). LC-MS retention time: 1.31 min; m/z (MH+): 615. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Example 1

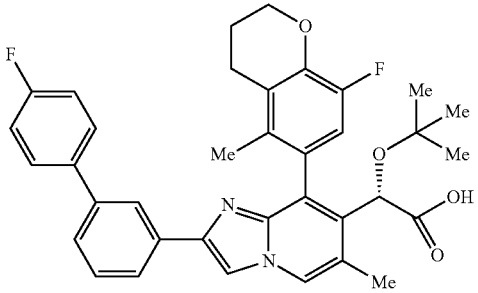 [SMILES: Cc1cn2cc(-c3cccc(-c4ccc(F)cc4)c3)nc2c(-c2cc(F)c3c(c2C)CCCO3)c1[C@H](OC(C)(C)C)C(=O)O]

(2S)-2-(tert-Butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetic acid NaOH (200 μl, 0.200 mmol, 1M aq) was added to a stirring solution of (2S)-ethyl 2-(tert-butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetate (13 mg, 0.020 mmol) in THF (400 μl) and MeOH (400 μl) at rt. The reaction was warmed to 65° C. and allowed to stir for 4 h. The mixture was then diluted with EtOAc and washed with 1M aq HCl, and sat aq NaCl. The organic phase was concentrated, diluted with MeOH and was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time=2.12 min. LCMS (M+H)=596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time=3.06 min. LCMS (M+H)=596 Proton NMR was acquired in deuterated DMSO. NMR of 1st/faster eluting atropisomer: $^1$H NMR (600 MHz, DMSO-d6) δ 8.40 (s, 1H), 8.26 (s, 1H), 7.99 (s, 1H), 7.78 (d, J=7.7 Hz, 1H), 7.74-7.69 (m, 2H), 7.51 (s, 1H), 7.48-7.42 (m, 1H), 7.29 (t, J=8.4 Hz, 2H), 6.84-6.78 (m, 1H), 4.78 (br. s., 1H), 4.27-4.19 (m, J=3.7 Hz, 2H), 2.72-2.66 (m, 2H), 2.40 (s, 3H), 2.08-2.01 (m, 2H), 1.83 (s, 3H), 1.03 (s, 9H).

Example 2

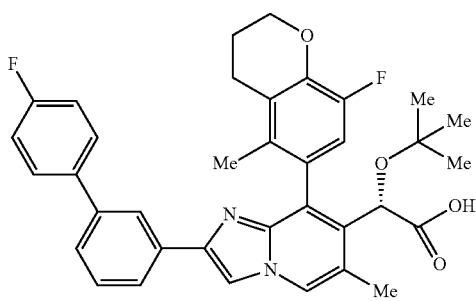 [SMILES: Cc1cn2cc(-c3cccc(-c4ccc(F)cc4)c3)nc2c(-c2cc(F)c3c(c2C)CCCO3)c1[C@H](OC(C)(C)C)C(=O)O]

The yield of the second eluting atropisomer product was 2.2 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time=2.21 min. LCMS (M+H)=596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time=3.10 min. LCMS (M+H)=597. Proton NMR was acquired in deuterated DMSO. NMR of 2nd/slower elueting atropisomer: $^1$H NMR (600 MHz, DMSO-d6) δ 8.39 (s, 1H), 8.26 (s, 1H), 8.02 (s, 1H), 7.81 (d, J=7.7 Hz, 1H), 7.72 (t, J=6.2 Hz, 2H), 7.53 (d, J=7.7 Hz, 1H), 7.48-7.43 (m, 1H), 7.29 (t, J=8.4 Hz, 2H), 7.27-7.18 (m, 1H), 4.92 (s, 1H), 4.29-4.16 (m, 2H), 2.76-2.62 (m, 2H), 2.34 (s, 3H), 2.10-2.00 (m, 2H), 1.80 (s, 3H), 0.89 (s, 9H).

Example 3

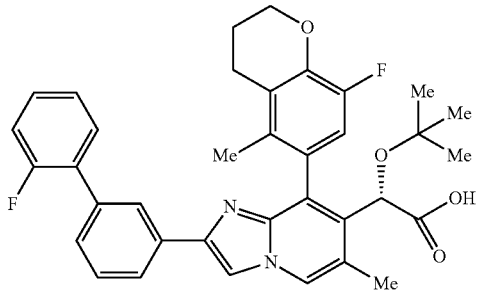 [SMILES: Cc1cn2cc(-c3cccc(-c4ccccc4F)c3)nc2c(-c2cc(F)c3c(c2C)CCCO3)c1[C@H](OC(C)(C)C)C(=O)O]

(2S)-2-(tert-Butoxy)-2-(8-(8-fluoro-5-methylchroman-6-yl)-2-(2'-fluoro-[1,1'-biphenyl]-3-yl)-6-methylimidazo[1,2-a]pyridin-7-yl)acetic acid Step 1: (2S)-Ethyl 2-(tert-butoxy)-2-(8-(8-fluoro-5-methylchroman-6-yl)-2-(2'-fluoro-[1,1'-biphenyl]-3-yl)-6-methylimidazo[1,2-a]pyridin-7-yl)acetate can be prepared in a similar manner as (2S)-ethyl 2-(tert-butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetate however using (2-fluorophenyl)boronic acid in place of (4-fluorophenyl) boronic acid.

Step 2: NaOH (0.4 ml, 0.4 mmol) (1M aq) was added to a stirring solution of (2S)-ethyl 2-(tert-butoxy)-2-(8-(8-fluoro-5-methylchroman-6-yl)-2-(2'-fluoro-[1,1'-biphenyl]-3-yl)-6-methylimidazo[1,2-a]pyridin-7-yl)acetate (25 mg, 0.040 mmol) in THF (0.8 ml) and MeOH (0.8 ml) at 60° C. The reaction was allowed to stir 12 h overnight. The mixture was diluted with EtOAc and washed with 1M HCl, and sat NaCl. The organic phase was concentrated and diluted with MeOH/DMF and the crude material was purified via preparative LC/MS with the following conditions: Column: Waters XBridge C18, 19×200 mm, 5-μm particles; Mobile Phase A: water with 10-mM ammonium acetate; Mobile Phase B: 95:5 methanol:water with 10-mM ammonium acetate; Gradient: 50-100% B over 15 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time: 2.07. M+H=597. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time: 3.01. M+H=597. Proton NMR was acquired in deuterated DMSO. $^1$H NMR (500 MHz, DMSO-d6) δ 8.38 (s, 1H), 8.30 (s, 1H), 7.91 (s, 1H), 7.83 (d, J=7.7 Hz, 1H), 7.54 (t, J=7.5 Hz, 1H), 7.51-7.46 (m, 1H), 7.45-7.39 (m, 2H), 7.35-7.28 (m, 2H), 6.82 (d, J=11.4 Hz, 1H), 4.85 (s, 1H), 4.27-4.16 (m, 2H), 2.72-2.65 (m, 2H), 2.39 (s, 3H), 2.08-2.00 (m, 2H), 1.81 (s, 3H), 1.04 (s, 9H).

(2S)-2-(tert-butoxy)-2-(2-(2'-fluoro-[1,1'-biphenyl]-3-yl)-8-(2-fluorophenyl)-6-methylimidazo[1,2-a]pyridin-7-yl)acetic acid was also isolated from the above reaction. This acid resulted from the minor impurity, unreacted ((S)-ethyl 2-(8-bromo-2-(3-chlorophenyl)-6-methylimidazo[1,2-a]pyridin-7-yl)-2-(tert-butoxy)acetate), which underwent bis Suzuki coupling in the presence of (2-fluorophenyl)boronic acid, thus forming (2S)-ethyl 2-(tert-butoxy)-2-(2-(2'-fluoro-[1,1'-biphenyl]-3-yl)-8-(2-fluorophenyl)-6-methylimidazo[1,2-a]pyridin-7-yl)acetate. When this ester was subjected to the hydrolysis conditions (2S)-2-(tert-butoxy)-2-(2-(2'-fluoro-[1,1'-biphenyl]-3-yl)-8-(2-fluorophenyl)-6-methylimidazo[1,2-a]pyridin-7-yl)acetic acid was formed.

Example 4

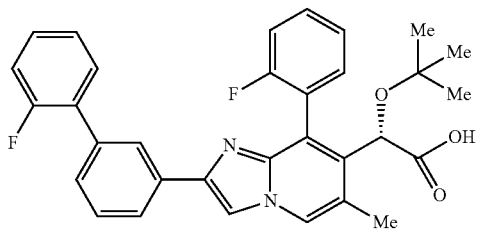 [SMILES: Cc1cn2cc(-c3cccc(-c4ccccc4F)c3)nc2c(-c2ccccc2F)c1[C@H](OC(C)(C)C)C(=O)O]

(2S)-2-(tert-Butoxy)-2-(2-(2'-fluoro-[1,1'-biphenyl]-3-yl)-8-(2-fluorophenyl)-6-methylimidazo[1,2-a]pyridin-7-yl)acetic acid The yield of this product was 2.5 mg, and its estimated purity by LCMS analysis was 94%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time: 1.91; M+H=527. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time: 2.89; M+H=527. Proton NMR was acquired in deuterated DMSO. $^1$H NMR (500 MHz, DMSO-d6) δ 8.40 (s, 1H), 8.33 (s, 1H), 7.96-7.91 (m, 1H), 7.85 (d, J=7.7 Hz, 1H), 7.67-7.62 (m, 1H), 7.60-7.51 (m, 2H), 7.51-7.45 (m, 1H), 7.43 (d, J=7.0 Hz, 2H), 7.38 (t, J=8.1 Hz, 2H), 7.34-7.29 (m, 2H), 4.94 (s, 1H), 2.34 (s, 3H), 0.88 (s, 9H).

Example 5

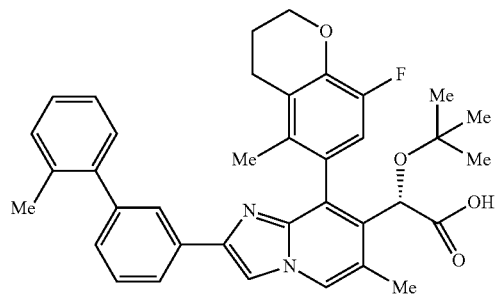 [SMILES: Cc1ccccc1-c1cccc(-c2cn3cc(C)c([C@H](OC(C)(C)C)C(=O)O)c(-c4cc(F)c5c(c4C)CCCO5)c3n2)c1]

(2S)-2-(tert-Butoxy)-2-(8-(8-fluoro-5-methylchroman-6-yl)-6-methyl-2-(2'-methyl-[1,1'-biphenyl]-3-yl)imidazo[1,2-a]pyridin-7-yl)acetic acid (2S)-Ethyl 2-(tert-butoxy)-2-(2-(3-chlorophenyl)-8-(8-fluoro-5-methylchroman-6-yl)-6-methylimidazo[1,2-a]pyridin-7-yl)acetate (18 mg, 0.032 mmol), o-tolylboronic acid (13 mg, 0.096 mmol), PdOAc$_2$ (0.71 mg, 3.2 μmol), dicyclohexyl(2',6'-dimethoxy-[1,1'-biphenyl]-2-yl)phosphine (2.6 mg, 6.4 μmol), cesium carbonate (20 mg, 0.064 mmol) were combined dry, degassed, backfilled with N$_2$, and taken up in DMF (0.6 ml) and water (60 μl) at rt. The reaction was heated at 80° C. and allowed to stir for 1 h. The mixture was then diluted with EtOAc and washed with H$_2$O, and sat aq NaCl. The organic phase was concentrated and taken up in 1 mL of MeOH, 1mL of THF and 0.5 mL of 1M NaOH and the mixture was stirred for 16 h overnight at 60° C. The mixture was then diluted with EtOAc and washed with 1M HCl, and sat NaCl. The organic phase was concentrated to afford a crude mixture of atropisomers. The crude material was purified via preparative LC/MS with the following conditions: Column: XBridge C18, 19×mm, 5-μm particles. Mobile Phase A: 5:95 acetonitrile: water with 10-mM ammonium acetate; Mobile Phase B: 95:5 acetonitrile: water with 10-mM ammonium acetate; Gradient: 40-80% B over 30 minutes, then a 5-minute hold at 100% B; Flow: 20 mL/min. Fractions containing the desired product were combined and dried via centrifugal evaporation.

The yield of the first eluting isomer was 1.3 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time: 2.12; M+H=593. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time: 3.09; M+H=593. Proton NMR was acquired in deuterated DMSO. $^1$H NMR (500 MHz, DMSO-d6) δ 8.37 (s, 1H), 8.28 (s, 1H), 7.78 (d, J=7.7 Hz, 1H), 7.70 (s, 1H), 7.43 (t, J=7.7 Hz, 1H), 7.32-7.19 (m, 5H), 6.81 (d, J=11.4 Hz, 1H), 4.86 (s, 1H), 4.26-4.15 (m, 2H), 2.71-2.65 (m, 2H), 2.39 (s, 3H), 2.21 (s, 3H), 2.08-1.99 (m, 2H), 1.80 (s, 3H), 1.04 (s, 9H).

Example 6

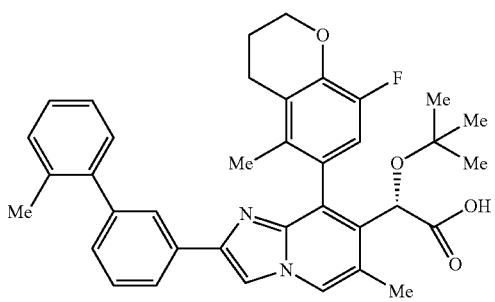 [SMILES: Cc1ccccc1-c1cccc(-c2cn3cc(C)c([C@H](OC(C)(C)C)C(=O)O)c(-c4cc(F)c5c(c4C)CCCO5)c3n2)c1]

The yield of the second eluting isomer was 3.2 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile: water with 10 mM ammonium acetate; Mobile Phase B: 95:5 acetonitrile:water with 10 mM ammonium acetate; Temperature:50° C.; Gradient: 0% B, 0-100% B over 3 minutes, then a 0.5-minute hold at 100% B; Flow: 1 mL/min; Detection: UV at 220 nm. Retention time: 2.23; M+H=593. Injection 2 conditions: Column: Waters BEH C18, 2.0×50 mm, 1.7-μm particles; Mobile Phase A: 5:95 methanol:water with 10 mM ammoniumacetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time: 3.14; M+H=593. Proton NMR was acquired in deuterated DMSO. ¹H NMR (500 MHz, DMSO-d6) δ 8.36 (s, 1H), 8.29 (s, 1H), 7.81 (d, J=7.7 Hz, 1H), 7.74 (s, 1H), 7.44 (t, J=7.7 Hz, 1H), 7.32-7.20 (m, 5H), 7.08 (d, J=11.7 Hz, 1H), 4.97 (s, 1H), 4.29-4.15 (m, 2H), 2.72-2.60 (m, 2H), 2.32 (s, 3H), 2.23 (s, 3H), 2.08-2.00 (m, 2H), 1.79 (s, 3H), 0.90 (s, 9H).

Example 7

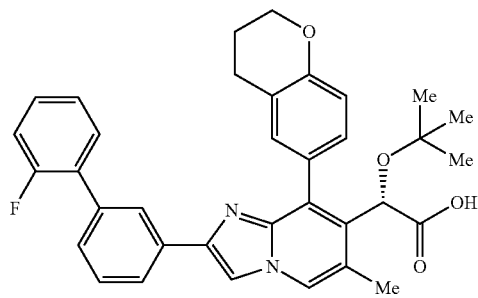 [SMILES: Cc1cn2cc(-c3cccc(-c4ccccc4F)c3)nc2c(-c2ccc3c(c2)CCCO3)c1[C@H](OC(C)(C)C)C(=O)O]

(S)-2-(tert-Butoxy)-2-(8-(chroman-6-yl)-2-(2'-fluoro [1,1'-biphenyl]-3-yl)-6-methylimidazo[1,2-a]pyridin-7-yl)acetic acid (S)-Methyl 2-(tert-butoxy)-2-(8-(chroman-6-yl)-2-(2'-fluoro-[1,1'-biphenyl]-3-yl)-6-methylimidazo[1,2-a]pyridin-7-yl)acetate (20 mg, 0.035 mmol) was dissolved in a 1:1:1: mixture of 1M NaOH/THF/MeOH. The solution was heated to 60° C. and stirred at this temperature overnight. The mixture was then diluted with EtOAc and sat aq NH₄Cl. The layers were separated and the aq layer was extracted with EtOAc (2×10 mL). The combined organic extracts were washed with water, dried over Na₂SO₄, filtered and concentrated to give a yellow oil. This oil was taken up in MeOH and was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time=2.12 min. LCMS (M+H)=596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time=1.20 min. LCMS (M+H)=565. Proton NMR was acquired in deuterated DMSO: ¹H NMR (500 MHz, DMSO-d6) δ 8.38 (s, 1H), 8.25 (s, 1H), 7.98 (br. s., 1H), 7.88 (d, J=7.7 Hz, 1H), 7.61-7.54 (m, 1H), 7.54-7.39 (m, 3H), 7.39-7.23 (m, 4H), 6.88 (d, J=8.4 Hz, 1H), 5.18 (s, 1H), 4.21 (m, 2H), 2.76 (m, 2H), 2.31 (s, 3H), 1.98 (d, J=4.4 Hz, 2H), 0.87 (s, 9H).

Example 8

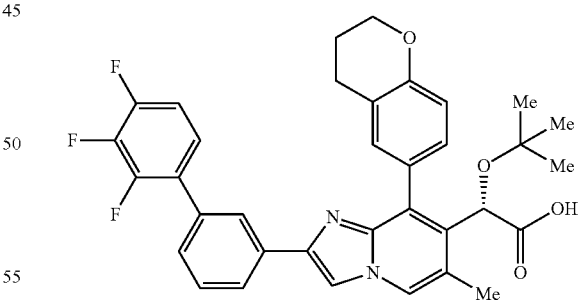

(S)-2-(tert-Butoxy)-2-(8-(chroman-6-yl)-6-methyl-2-(2',3',4'-trifluoro-[1,1'-biphenyl]-3-yl)imidazo[1,2-a]pyridin-7-yl)acetic acid (S)-Methyl 2-(tert-butoxy)-2-(8-(chroman-6-yl)-2-(2'-fluoro-[1,1'-biphenyl]-3-yl)-6-methylimidazo[1,2-a]pyridin-7-yl)acetate (20 mg, 0.035 mmol) was dissolved in a 1:1:1: mixture of 1M NaOH/THF/MeOH. The solution was heated to 60° C. and stirred at this temperature overnight.

The mixture was then diluted with EtOAc and sat aq NH4Cl. The layers were separated and the aq layer was extracted with EtOAc (2×10 mL). The combined organic extracts were washed with water, dried over $Na_2SO_4$, filtered and concentrated to give a yellow oil. This oil was taken up in MeOH and was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-90% B over 30 minutes, then a 5-minute hold at 100% B; Flow: 20 mL/min. Fractions containing the desired product were combined and dried via centrifugal evaporation. The yield of the product was 9.9 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time=2.12 min. LCMS (M+H)=596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time=1.24 min. LCMS (M+H)=601 Proton NMR was acquired in deuterated DMSO: $^1H$ NMR (500 MHz, DMSO-d6) δ 8.38 (s, 1H), 8.24 (s, 1H), 7.96 (d, J=13.2 Hz, 1H), 7.92 (d, J=8.1 Hz, 1H), 7.56-7.49 (m, 1H), 7.44 (d, J=5.9 Hz, 3H), 7.37-7.25 (m, 2H), 6.87 (d, J=8.1 Hz, 1H), 5.15 (s, 1H), 4.21 (m 2H), 2.84-2.71 (m, 2H), 2.31 (s, 3H), 1.97 (d, J=7.0 Hz, 2H), 0.86 (s, 9H).

Example 9

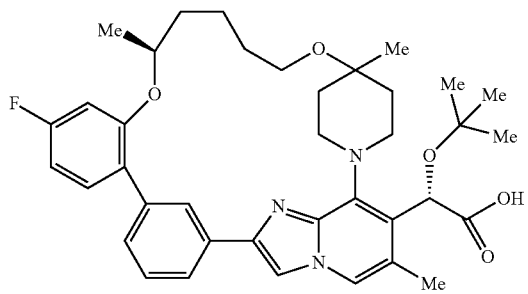 [SMILES: Cc1cn2cc3nc2c(c1[C@H](OC(C)(C)C)C(=O)O)N1CCC(C)(CC1)OCCCC[C@H](C)Oc1cc(F)ccc1-c1cccc-3c1]

(2S)-2-(tert-Butoxy)-2-[(22S)-18-fluoro-4,22,28-trimethyl-21,27-dioxa-1,6,8-triazahexacyclo[26.2.2.1$^{6,9}$.1$^{10,14}$.0$^{2,7}$.0$^{15,20}$]tetratriaconta-2,4,7,9(34),10(33),11,13,15,17,19-decaen-3-yl]acetic acid NaOH (0.2 ml, 0.2 mmol, 1 M aq) was added to a stirring mixture of ethyl (2S)-tert-butoxy[(22S)-18-fluoro-4,22,28-trimethyl-21,27-dioxa-1,6,8-triazahexacyclo[26.2.2.16,9.110,14.02,7.015,20]tetratriaconta-2,4,7,9(34),10(33),11,13,15,17,19-decaen-3-yl]acetate (15 mg, 0.022 mmol) in THF (0.5 ml) and MeOH (0.5 ml) at rt. The reaction mixture was allowed to stir at 65° C. for 6 h then allowed to cool to rt and stir for 16 h overnight. The reaction was then warmed back up to 65° C. and stirred for 4 h. The reaction was taken up in EtOAc and washed with aq 1M HCl and brine. The organic phase was concentrated and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time: 2.54, M+H=643. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time=3.35, M+H=644. Proton NMR was acquired in deuterated DMSO. $^1H$ NMR (500 MHz, DMSO-d6) δ 8.45 (s, 1H), 8.30 (s, 1H), 8.07 (s, 1H), 7.78 (d, J=7.7 Hz, 1H), 7.43 (t, J=7.7 Hz, 1H), 7.29 (t, J=7.7 Hz, 1H), 7.18 (d, J=7.3 Hz, 1H), 7.09 (d, J=9.9 Hz, 1H), 6.86-6.76 (m, 1H), 6.17 (br. s., 1H), 4.74-4.64 (m, 2H), 3.49-3.25 (m, 5H), 3.05 (d, J=9.2 Hz, 1H), 2.58 (d, J=11.7 Hz, 1H), 2.23 (s, 3H), 2.04-1.95 (m, 1H), 1.93-1.82 (m, 2H), 1.78-1.57 (m, 4H), 1.56-1.45 (m, 2H), 1.46-1.38 (m, 1H), 1.17-1.12 (m, 12H), 1.09-1.05 (m, 3H).

Example 10

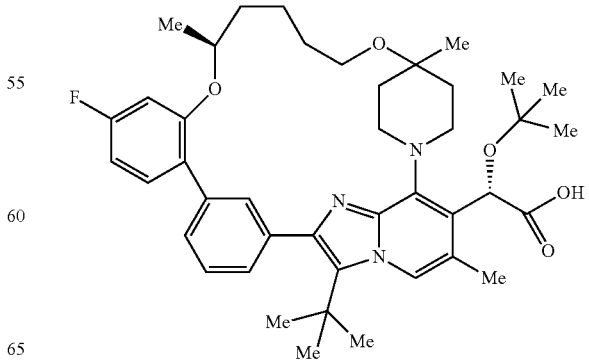

(2S)-2-(tert-Butoxy)-2-[(22S)-34-tert-butyl-18-fluoro-4,22,28-trimethyl-21,27-dioxa-1,6,8-triazahexacyclo[26.2.2.1$^{6,9}$.1$^{10,14}$.0$^{2,7}$.0$^{15,20}$]tetratriaconta-2,4,7,9 (34),10(33),11,13,15,17,19-decaen-3-yl] acetic acid Step 1: Preparation of ethyl (S)-2-(tert-butoxy)-2-((S,Z)-23-(tert-butyl)-44-fluoro-14,26,6-trimethyl-5,11-dioxa-2(8,2)-imidazo[1,2-a]pyridina-1(1,4)-piperidina-3(1,3),4(1,2)-dibenzenacycloundecaphane-27-yl)acetate 2-Bromo-2-methylpropane (45 µl, 0.39 mmol) was added to a stirring slurry of ethyl (2S)-[(22S)-18-fluoro-4,22,28-trimethyl-21,27-dioxa-1,6,8-triazahexacyclo[26.2.2.16, 9.110,14.02,7.015,20]tetratriaconta-2,4,7,9(34),10(33),11, 13,15,17,19-decaen-3-yl](hydroxy)acetate (40 mg, 0.065 mmol) and silver oxide (45 mg, 0.20 mmol) in dichloromethane (1.3 ml) and cyclohexane (1.3 ml) at rt under $N_2$ balloon. The reaction was allowed to stir 4 h. Then an additional aliquot of reagents: silver oxide (45 mg, 0.20 mmol) and 2-bromo-2-methylpropane (45 µl, 0.39 mmol) were added and the reaction was allowed to stir for 3 days at 35° C. The reaction was concentrated, adsorbed onto Celite and purified on silica gel (Biotage, EtOAc/hexanes gradient, fraction collection at λ=254 nm) to give the expected product (5.0 mg, 6.9 µmol, 11% yield). LC-MS retention time: 1.55 min; m/z (MH+): 728. LC data was recorded on a Shimadzu LC-10AS liquid chromatograph equipped with a Waters Aquity BEH C18 2.1×50 mm 1.7 um column using a SPD-10AV UV-Vis detector at a detector wave length of 220 nM. The elution conditions employed a flow rate of 0.8 mL/min, a gradient of 98% solvent A/2% solvent B to 98% solvent A/2% solvent B, a gradient time of 1.5 min, a hold time of 0.5 min, and an analysis time of 2 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Step 2

NaOH (206 µl, 0.206 mmol) was added to a stirring mixture of ethyl (S)-2-(tert-butoxy)-2-((S,Z)-23-(tert-butyl)-44-fluoro-14,26,6-trimethyl-5,11-dioxa-2(8,2)-imidazo[1,2-a]pyridina-1(1,4)-piperidina-3(1,3),4(1,2)-dibenzenacycloundecaphane-27-yl)acetate (15 mg, 0.021 mmol) in THF (0.4 ml) and MeOH (0.4 ml) at rt. The reaction was allowed to stir at 65° C. for 16 h. The mixture was then diluted with EtOAc and washed with aq 1M HCl, and sat aq NaCl. The organic phase was concentrated and the residue was taken up in DMF and the crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 70-90% B over 30 minutes, then a 15-minute hold at 100% B; Flow: 20 mL/min. Fractions containing the desired product were combined and dried via centrifugal evaporation. The yield of the product was 1.4 mg, and its estimated purity by LCMS analysis was 99%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Retention time: 2.94 min. M+H=699. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm. Retention time: 2.54 min. M+H=699. Proton NMR was acquired in deuterated DMSO. $^1$H NMR (500 MHz, DMSO-d6) δ 8.09 (s, 1H), 7.51 (s, 1H), 7.39-7.25 (m, 4H), 7.05-6.96 (m, 1H), 6.81 (td, J=8.3, 2.2 Hz, 1H), 6.17 (s, 1H), 4.50-4.34 (m, 2H), 3.53-3.45 (m, 1H), 3.33-3.24 (m, 2H), 3.07-2.98 (m, 1H), 2.65-2.56 (m, 1H), 2.32 (s, 3H), 1.92-1.84 (m, 1H), 1.73-1.52 (m, 4H), 1.50-1.38 (m, 4H), 1.36-1.27 (m, 10H), 1.20-1.15 (m, 12H), 1.12 (s, 3H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I or Formula II

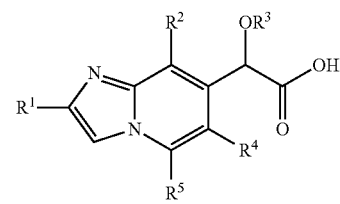

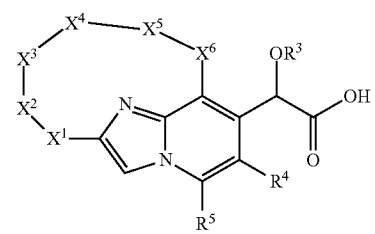

where:
$R^1$ is phenyl substituted with 0-3 substituents selected from halo, alkyl, haloalkyl, alkenyl, $Ar^1$, ($Ar^1$)alkyl, and ($Ar^1$)O;

$R^2$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or $R^2$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

$R^3$ is alkyl or haloalkyl;

R⁴ is alkyl;
R⁵ is hydrogen or alkyl;
Ar¹ is phenyl or pyridinyl and is substituted with 0-3 substituents selected from halo, cyano, alkyl, haloalkyl, alkoxy, haloalkoxy, and alkenyloxy;
X¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;
X² is phenyl substituted with 0-3 substituents selected from halo, alkyl, haloalkyl, alkoxy, and haloalkoxy;
X³ is O or absent;
X⁴ is alkylene or alkenylene;
X⁵ is O or absent; and
X⁶ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

2. A compound of claim 1 according to Formula I where R¹ is phenyl substituted with 0-3 substituents selected from halo, alkyl, haloalkyl, alkenyl, Ar¹, (Ar¹)alkyl, and (Ar¹)O; R² is piperidinyl substituted with 0-3 alkyl substituents or R² is chromanyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; R³ is alkyl; R⁴ is alkyl; R⁵ is hydrogen; and Ar¹ is phenyl substituted with 0-3 substituents selected from halo, cyano, alkyl, haloalkyl, alkoxy, haloalkoxy, and alkenyloxy; or a pharmaceutically acceptable salt thereof.

3. A compound of claim 1 according to Formula II where X¹ is phenyl; X² is phenyl substituted with 0-3 substituents selected from halo, alkyl, haloalkyl, alkoxy, and haloalkoxy; X³ is O or absent; X⁴ is alkylene or alkenylene; X⁵ is O or absent; and X⁶ is piperidinyl substituted with 0-3 alkyl substituents; or a pharmaceutically acceptable salt thereof.

4. A compound of claim 1 where R¹ is phenyl substituted with 1 Ar¹ substituent.

5. A compound of claim 1 where R² is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

6. A compound of claim 1 where Ar¹ is phenyl substituted with 0-3 substituents selected from halo, cyano, alkyl, haloalkyl, alkoxy, haloalkoxy, and alkenyloxy.

7. A compound of claim 1 where X¹ is phenyl.

8. A compound of claim 1 where X⁶ is piperidinyl substituted with 0-3 halo or alkyl substituents.

9. A compound of claim 1 selected from the group consisting of
(2S)-2-(tert-Butoxy)-2-(8-(8-fluoro-5-methylchroman-6-yl)-2-(4'-fluoro-[1,1'-biphenyl]-3-yl)-6-methylimidazo[1,2-a]pyridin-7-yl)acetic acid;
(2S)-2-(tert-Butoxy)-2-(8-(8-fluoro-5-methylchroman-6-yl)-2-(2'-fluoro-[1,1'-biphenyl]-3-yl)-6-methylimidazo[1,2-a]pyridin-7-yl)acetic acid;
(2S)-2-(tert-Butoxy)-2-(2-(2'-fluoro-[1,1'-biphenyl]-3-yl)-8-(2-fluorophenyl)-6-methylimidazo[1,2-a]pyridin-7-yl)acetic acid;
(2S)-2-(tert-Butoxy)-2-(8-(8-fluoro-5-methylchroman-6-yl)-6-methyl-2-(2'-methyl-[1,1'-biphenyl]-3-yl)imidazo[1,2-a]pyridin-7-yl)acetic acid;
(S)-2-(tert-Butoxy)-2-(8-(chroman-6-yl)-2-(2'-fluoro-[1,1'-biphenyl]-3-yl)-6-methylimidazo[1,2-a]pyridin-7-yl)acetic acid;
(S)-2-(tert-Butoxy)-2-(8-(chroman-6-yl)-6-methyl-2-(2',3',4'-trifluoro-[1,1'-biphenyl]-3-yl)imidazo[1,2-a]pyridin-7-yl)acetic acid;
(2S)-2-(tert-butoxy)-2-[(22S)-18-fluoro-4,22,28-trimethyl-21,27-dioxa-1,6,8-triazahexacyclo[26.2.2.1⁶,⁹.1¹⁰,¹⁴.0²,⁷.0¹⁵,²⁰]tetratriaconta-2,4,7,9(34),10(33),11,13,15,17,19-decaen-3-yl]acetic acid; and
(2S)-2-(tert-Butoxy)-2-[(22S)-34-tert-butyl-18-fluoro-4,22,28-trimethyl-21,27-dioxa-1,6,8-triazahexacyclo[26.2.2.1⁶,⁹.1¹⁰,¹⁴.0²,⁷.0¹⁵,²⁰]tetratriaconta-2,4,7,9(34),10(33),11,13,15,17,19-decaen-3-yl]acetic acid;
or a pharmaceutically acceptable salt thereof.

10. A composition useful for treating HIV infection comprising a therapeutic amount of a compound of claim 1 or a pharmaceutically acceptable salt thereof and a pharmaceutically acceptable carrier.

11. A method for treating HIV infection comprising administering a therapeutically effective amount of a compound of claim 1, or a pharmaceutically acceptable salt thereof, to a patient.

* * * * *